(12) United States Patent
Higuchi

(10) Patent No.: US 9,872,610 B2
(45) Date of Patent: *Jan. 23, 2018

(54) IMAGE PROCESSING DEVICE, IMAGING DEVICE, COMPUTER-READABLE STORAGE MEDIUM, AND IMAGE PROCESSING METHOD

(71) Applicant: OLYMPUS CORPORATION, Tokyo (JP)

(72) Inventor: Keiji Higuchi, Kunitachi (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/790,308

(22) Filed: Jul. 2, 2015

(65) Prior Publication Data
US 2015/0297068 A1 Oct. 22, 2015

Related U.S. Application Data

(63) Continuation of application No. 12/732,774, filed on Mar. 26, 2010, now Pat. No. 9,101,288.

(30) Foreign Application Priority Data

Mar. 26, 2009 (JP) .................... 2009-077564

(51) Int. Cl.
*A61B 1/04* (2006.01)
*A61B 1/00* (2006.01)
(Continued)

(52) U.S. Cl.
CPC ............ *A61B 1/043* (2013.01); *A61B 1/0051* (2013.01); *A61B 1/00096* (2013.01); *A61B 1/05* (2013.01);
(Continued)

(58) Field of Classification Search
CPC ... A61B 1/00096; A61B 1/0638; A61B 1/043; A61B 1/0051; A61B 1/05; A61B 1/0646; H04N 5/2354; H04N 2005/2255
(Continued)

(56) References Cited

U.S. PATENT DOCUMENTS 3,596,653 A  8/1971 Hotchkiss
5,833,617 A  11/1998 Hayashi
(Continued)

FOREIGN PATENT DOCUMENTS

JP  2002-336187     11/2002
JP  2003-215469 A   7/2003
(Continued)

OTHER PUBLICATIONS

Notice of Rejection dated Jul. 9, 2013 from related Japanese Application No. 2009-077564, together with an English language translation.

*Primary Examiner* — Neil Mikeska
*Assistant Examiner* — Richard Carter
(74) *Attorney, Agent, or Firm* — Scully, Scott, Murphy & Presser, P.C.

(57) ABSTRACT

A reflected light image and a fluorescent light image of an observed region are acquired with an imaging system. A gradation level of the reflected light image is set on the basis of a feature value of the acquired reflected light image. The focus of the imaging system is controlled in accordance with the set gradation level. The fluorescent light image is corrected using a focus-controlled reflected light image of the observed region. Accordingly, the image of an object in the observed region from which the fluorescent light is generated is sharpened.

7 Claims, 11 Drawing Sheets

(51) Int. Cl.
*A61B 1/06* (2006.01)
*A61B 1/005* (2006.01)
*A61B 1/05* (2006.01)
*H04N 5/235* (2006.01)
*H04N 5/225* (2006.01)

(52) U.S. Cl.
CPC .......... *A61B 1/0638* (2013.01); *A61B 1/0646* (2013.01); *H04N 5/2354* (2013.01); *H04N 2005/2255* (2013.01)

(58) Field of Classification Search
USPC ...... 348/65, 68; 382/266; 600/160, 167, 178
See application file for complete search history.

(56) References Cited

U.S. PATENT DOCUMENTS

| | | | |
|---|---|---|---|
| 7,187,810 B2 | 3/2007 | Clune et al. | |
| 9,101,288 B2* | 8/2015 | Higuchi | A61B 1/00096 |
| 2002/0013512 A1* | 1/2002 | Sendai | A61B 5/0071 |
| | | | 600/160 |
| 2003/0179291 A1* | 9/2003 | Kobayashi | A61B 1/045 |
| | | | 348/65 |
| 2005/0093974 A1 | 5/2005 | Hibi et al. | |
| 2006/0058684 A1 | 3/2006 | Sendai | |
| 2007/0038029 A1* | 2/2007 | Ota | A61B 1/04 |
| | | | 600/167 |
| 2009/0016635 A1* | 1/2009 | Takayama | G06T 5/004 |
| | | | 382/266 |
| 2009/0105544 A1* | 4/2009 | Takahira | A61B 1/00188 |
| | | | 600/178 |
| 2009/0290017 A1 | 11/2009 | Shibasaki | |
| 2010/0194871 A1 | 8/2010 | Komukai | |

FOREIGN PATENT DOCUMENTS

| | | |
|---|---|---|
| JP | 2006-175052 A | 7/2006 |
| JP | 2008-173290 A | 7/2008 |

\* cited by examiner

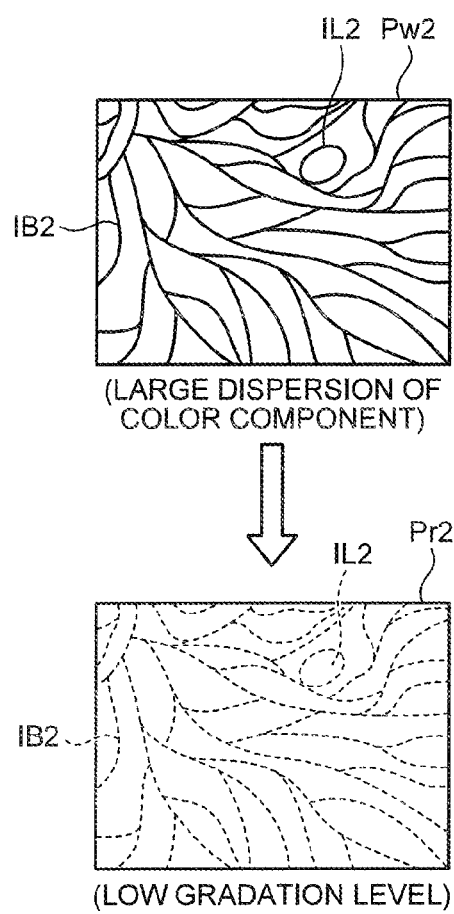

IMAGE PROCESSING DEVICE, IMAGING DEVICE, COMPUTER-READABLE STORAGE MEDIUM, AND IMAGE PROCESSING METHOD

CROSS-REFERENCE TO RELATED APPLICATIONS

The present application is a continuation application of U.S. Ser. No. 12/732,774, filed Mar. 26, 2010, which claims the benefit of priority from Japanese Patent Application No. 2009-077564, filed on Mar. 26, 2009, the entire contents of each of which are incorporated herein by reference.

BACKGROUND OF THE INVENTION

1. Field of the Invention

The present invention relates to an image processing device, an imaging device, a computer-readable storage medium, and an image processing method and particularly relates to an image processing device, an imaging device, a computer-readable storage medium, and an image processing method for processing a fluorescent light image based on the fluorescent light from an object.

2. Description of the Related Art

Endoscopes are used in the medical field to observe the internal organs of a subject. An elongated and flexible insertion unit of an endoscope is inserted into the body cavity of a subject, such as a patient. White light is applied to body tissue in the body cavity via the inserted flexible insertion unit. By receiving the light reflected from the body tissue with an imaging unit in the flexible insertion unit, a white light image of the body tissue is captured. The white light image of the body tissue is displayed on a display unit of the endoscope. A user, such as a doctor, observes the interior of the body cavity of the subject using the white light image of the body tissue that is displayed on the display unit of the endoscope.

In the field of endoscopy, endoscopes have also been used recently that allow fluorescence observation of an observed region, such as body tissue, in the body cavity. A fluorescence-observation endoscope applies excitation light to body tissue in the body cavity via a flexible insertion unit that is inserted into the body cavity. The endoscope captures a fluorescent light image of the body tissue by receiving, with its imaging unit in the flexible insertion unit, light of autofluorescence or drug fluorescence that is generated from the body tissue due to the application of excitation light. A user, such as a doctor, visually checks the fluorescent light image of the body tissue, which is captured as described above, using the display unit of the endoscope, and performs fluorescence observation of the observed region using the fluorescent light image of the body tissue. There are also apparatuses that acquire a normalization image based on light emitted from an observed region, such as body tissue, due to the application of light on the observed region, and that performs division regarding a fluorescent light image of the observed region using the normalization image in order to generate a normalized fluorescent light image (see, Japanese Laid-open Patent Publication No. 2002-336187).

In the conventional fluorescence observation, when the luminance of a fluorescent light image of an observed region, such as body tissue, is corrected by a normalization process, a white light image of the observed region is generally used as the normalization image and the luminance value of the fluorescent light image of the observed region is divided by the luminance value of the white light image.

SUMMARY OF THE INVENTION

An image processing device according to an aspect of the present invention includes an image acquiring unit that acquires a reflected light image and a fluorescent light image of an observed region, the reflected and the fluorescent light images being captured by an imaging system; a feature value calculating unit that calculates a feature value of the reflected light image acquired by the image acquiring unit; a gradation level setting unit that sets a gradation level of the reflected light image on the basis of the feature value; a control unit that controls a focus of the imaging system in accordance with the gradation level; and a corrected fluorescent light image generating unit that generates a corrected fluorescent light image that is obtained by correcting the fluorescent light image using a focus-controlled reflected light image of the observed region that is acquired by the image acquiring unit after the focus is controlled.

A computer-readable storage medium according to another aspect of the present invention stores therein an image processing program that contains instructions. The instructions cause a computer to perform acquiring a reflected light image of an observed region based on light that is reflected from the observed region; calculating a feature value of the reflected light image; setting a gradation level of the reflected light image on the basis of the feature mount; controlling a focus of an imaging system for the reflected light image in accordance with the gradation level; acquiring a focus-controlled reflected light image of the observed region after the focus is controlled; and generating a corrected fluorescent light image that is obtained by correcting the fluorescent light image of the observed region, using the focus-controlled reflected light image.

An image processing method according to still another aspect of the present invention includes acquiring a reflected light image of an observed region based on light that is reflected from the observed region; calculating a feature value of the reflected light image; setting a gradation level of the reflected light image on the basis of the feature mount; controlling a focus of an imaging system for the reflected light image in accordance with the gradation level; acquiring a focus-controlled reflected light image of the observed region after the focus is controlled; and generating a corrected fluorescent light image that is obtained by correcting the fluorescent light image of the observed region, using the focus-controlled reflected light image.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 7B is a schematic diagram specifically explaining the feature value calculation process and the gradation level setting process in a case where a white light image in which the vessel structure is dispersed is captured in the second embodiment of the present invention;

DETAILED DESCRIPTION OF THE PREFERRED EMBODIMENTS

Image processing devices, imaging devices, computer-readable storage media, and image processing methods according to some embodiments of the present invention are explanation in detail below with reference to the accompanying drawings. In the following description, endoscopes that capture an image of the interior of the body cavity of a subject, such as a patient, are explained as an example of an imaging device according to the present invention, and the image processing devices, the computer-readable storage media, and the image processing methods that are used for the endoscopes are explained. The present invention, however, is not limited to the embodiments.

First Embodiment

Figure 1:
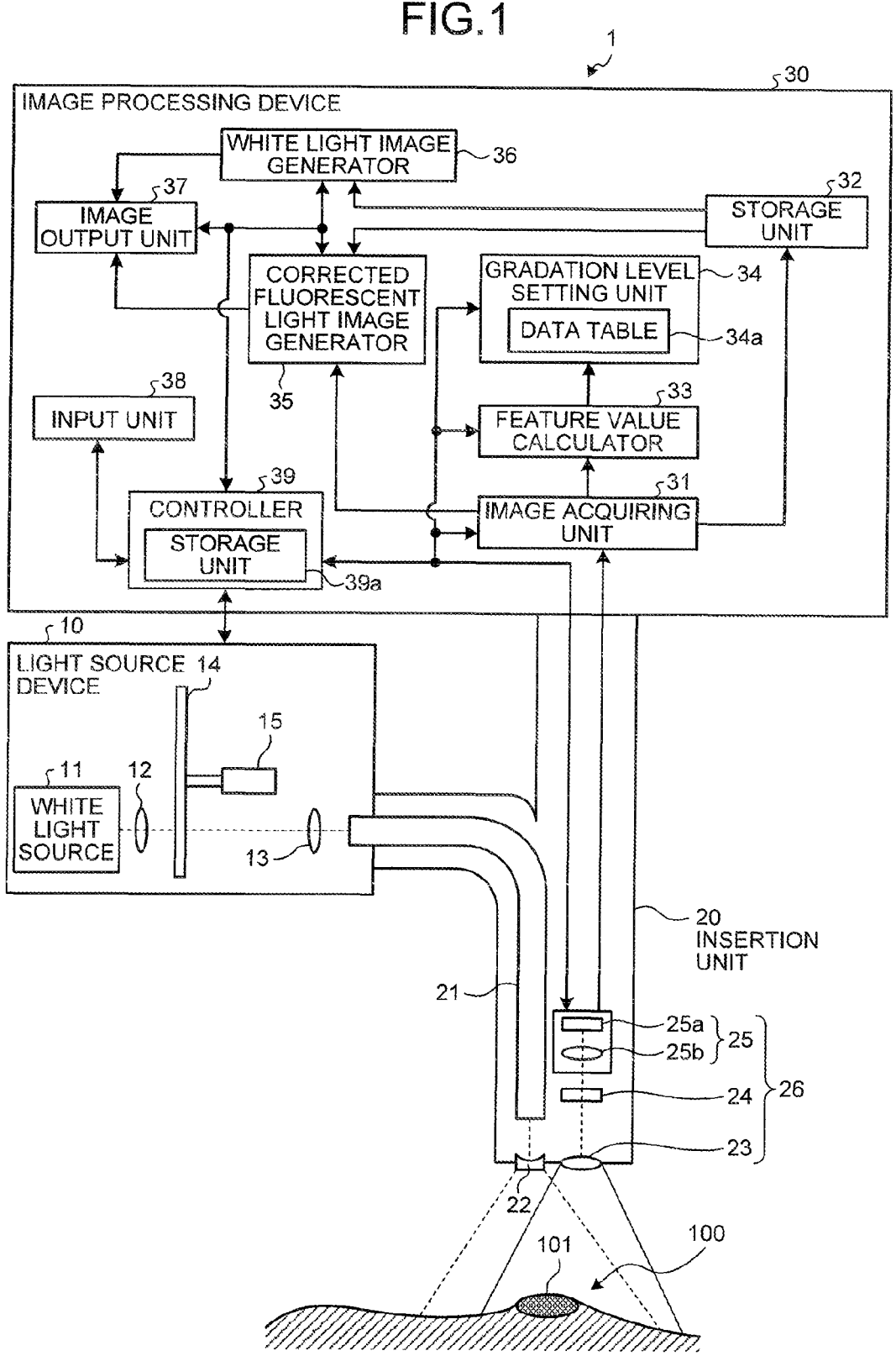
FIG. 1 is a block diagram schematically representing an example of a configuration of an endoscope according to a first embodiment of the present invention.

FIG. 1 is a block diagram schematically representing an example of a configuration of an endoscope according to a first embodiment of the present invention. An endoscope 1 according to the first embodiment is an example of an imaging device according to the present invention. As represented in FIG. 1, the endoscope 1 includes a light source device 10 that applies light to an observed region 100 in a subject, such as a patient; an elongated insertion unit 20 that is inserted into the body cavity of the subject; and an image processing device 30 that processes an image of the observed region 100.

The light source device 10 functions as a light source unit that applies excitation light for exciting a fluorescent agent and white light, which is an example of illuminating light that illuminates an object to the observed region 100.

Specifically, the light source device 10 includes a white light source 11; a collimating lens 12 that causes the light emitted from the white light source 11 to be approximately parallel light; a condenser lens 13 that concentrates the collimated light; a rotation filter 14 that switches the illuminating light to the observed region 100 from excitation light to white light or vise versa; and a motor 15 that is a driver of the rotation filter 14. The light source device 10 has a function of switching the light emitted between excitation light and white light alternately.

The white light source 11 is configured with a light source that can emit white light in a broadband covering the wavelength band of the excitation light that excites the fluorescent agent. Specifically, the power supply to the white light source 11 is turned on and off by operating the switch (not shown) of the light source device 10, and the light emitting timing is controlled by a controller 39 of the image processing device 30 to be described below. The white light that is emitted by the white light source 11 contains color lights of a blue color component (B), a green color component (G), and a red color component (R), and further contains excitation light that excites a fluorescent agent accumulated on a lesion 101, such as a tumor. The excitation light from the white light source 11 is of the wavelength band of visible light or lower (for example, of the wavelength band of ultraviolet) and excites the fluorescent agent accumulated on the lesion 101 to cause emission of fluorescent light in the wavelength band of visible light, for example, the wavelength band of 400 to 740 nm.

The collimating lens 12 is arranged in the optical path of the white light that is emitted from the white light source 11, and causes the white light from the white light source 11 to be approximately parallel light. The light that is collimated by the collimating lens 12 passes through the rotation filter 14, and then is concentrated by the condenser lens 13. The light that is concentrated by the condenser lens 13 is applied via the insertion unit 20 to the observed region 100 in the subject.

Figure 2:
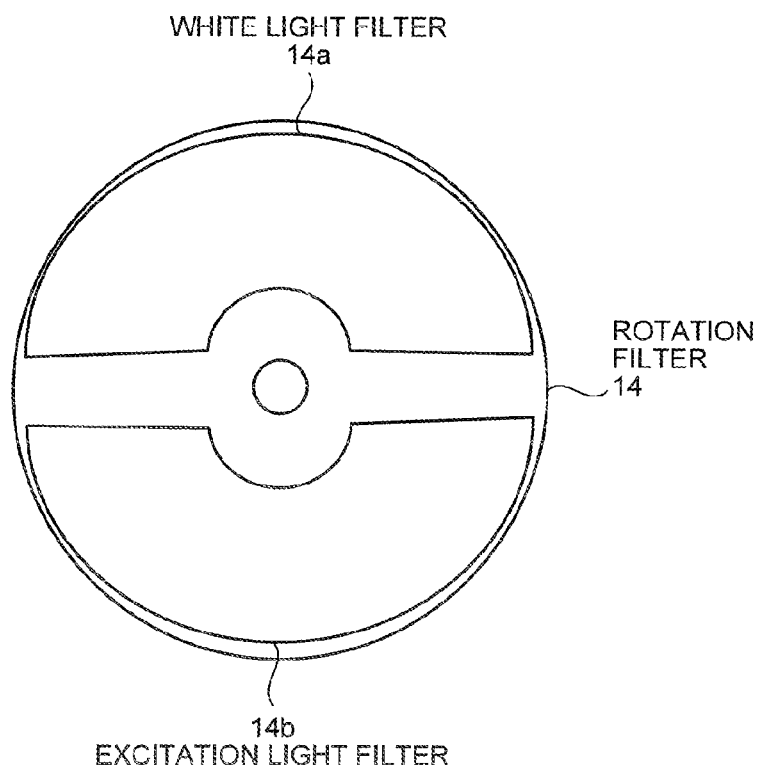
FIG. 2 is a schematic diagram representing an example of a configuration of a rotation filter according to the first embodiment of the present invention.
Figure 3:
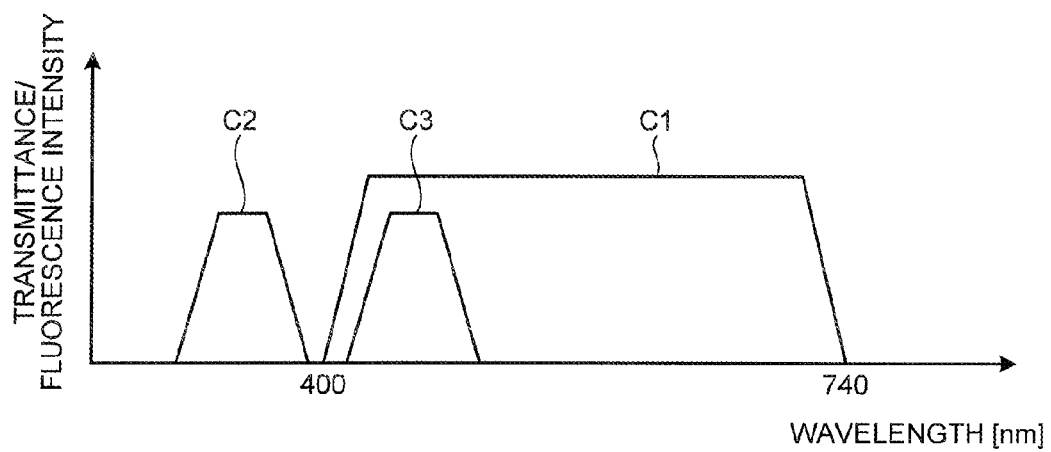
FIG. 3 is a schematic diagram representing an example of transmittance properties of the rotation filter according to the first embodiment of the present invention.

The rotation filter 14 extracts light in a predetermined wavelength band from the white light that is emitted by the white light source 11. FIG. 2 is a schematic diagram representing an example of transmittance properties of the rotation filter. FIG. 3 illustrates a correlation line C3 of wavelength with respect to intensity that illustrates the spectral properties of the fluorescent light that is generated due to the excitation light extracted by the rotation filter 14. As represented in FIG. 2, the rotation filter 14 includes a white light filter 14a and an excitation light filter 14b with different spectral properties.

The white light filter 14a allows white light in the predetermined wavelength band out of the white light, which is emitted by the white light source 11, to pass. Specifically, the white light filter 14a has transmittance properties that allow the white light in a wavelength band of 400 to 740 nm to pass as represented by the correlation line C1 of wavelength with respect to intensity represented in FIG. 3. The white light filter 14a with such transmittance properties extracts the white light in the wavelength band of 400 to 740 nm from the light emitted by the white light source 11 and allows the extracted white light to pass as the illuminating light to the observed region 100.

The excitation light filter 14b allows the excitation light in the predetermined wavelength band out of the white light that is emitted by the white light source 11 to pass. Specifically, the excitation light filter 14b has transmittance properties that allow light in the wavelength band of 400 nm or lower, for example, in the wavelength band of ultraviolet as represented by the correlation line C2 of wavelength with respect to intensity. The excitation light filter 14b with such transmittance properties extracts the excitation light in the wavelength band illustrated by the correlation line C2 represented in FIG. 3 from the white light that is emitted by the white light source 11 and allows the extracted excitation light to pass. The excitation light that is extracted by the excitation light filter 14b excites the fluorescent agent that is specifically accumulated on the lesion 101, such as a tumor, existing in the observed region 100 to cause generation of fluorescent light in the wavelength band of visible light, for example, in the wavelength band of 400 to 740 nm as illustrated by the correlation line C3 shown in FIG. 3.

The rotation filter 14 that includes the white light filter 14a and the excitation light filter 14b is driven by the motor 15 to rotate in the circumferential direction. This switches between the white light filter 14a and the excitation light filter 14b and positions them alternately in the optical path of the white light from the white light source 11 (see the dotted line in the light source device 10 represented in FIG. 1). In the state where the white light filter 14a is positioned in the optical path, the rotation filter 14 allows the white light of 400 to 740 nm to pass. In the state where the excitation light filter 14b is positioned in the optical path, the rotation filter 14 allows the excitation light in the wavelength band of the white light to pass. In other words, the rotation filter 14 allows white light and excitation light to pass alternately.

The insertion unit 20 is an elongated flexible structure that can be inserted into the body cavity of the subject, and can be curved in a desired direction in response to the operation of an operating unit (not shown) of the endoscope 1. As represented in FIG. 1, the base side of the insertion unit 20 is connected to the light source device 10 and the image processing device 30, and the insertion unit 20 includes a light guide fiber 21 that guides the light emitted from the light source device 10 to the tip portion; and a lens 22 that diffuses the light that is guided by the light guide fiber 21. The insertion unit 20 further includes an imaging system 26 that captures a reflected light image and a fluorescent light image of the observed region 100.

The light guide fiber 21 is configured with optical fibers. The light guide fiber 21 propagates the white light and the excitation light that are emitted alternately by the light source device 10 to the tip portion of the insertion unit 20 sequentially. The white light and the excitation light from the light source device 10 that are sequentially guided by the light guide fiber 21 are diffused sequentially by the lens 22 and then are alternately applied to the observed region 100 in the subject.

The white light from the light source device 10 that is applied to the observed region 100 illuminates the observed region 100 and is reflected on the observed region 100. When the lesion 101 on which the fluorescent agent is accumulated previously exists in the observed region 100, the excitation light that is applied to the observed region 100 at the timing different from that of the white light excites the fluorescent agent on the lesion 101 in order to cause generation of, for example, the fluorescent light in the wavelength band of the white light.

The imaging system 26 is used to capture a reflected light image and a fluorescent light image of the observed region 100. The imaging system 26 includes an objective lens 23 that concentrates the reflected light or the fluorescent light from the observed region 100; a barrier filter 24 that cuts off the excitation light out of the concentrated light from the observed region 100; and an imaging unit 25 that captures the white light image and the fluorescent light image of the observed region 100.

The objective lens 23 concentrates the reflected light and the fluorescent light from the observed region 100. Specifically, when the white light from the light source device 10 is applied to the observed region 100, the objective lens 23 concentrates the white light reflected from the observed region 100. When the excitation light from the light source device 10 is applied to the observed region 100, the objective lens 23 concentrates the fluorescent light that is generated from the observed region 100 (specifically, the lesion 101) and the excitation light that is reflected from the observed region 100.

The barrier filter 24 is used to cut off the excitation light contained in the light from the observed region 100. Specifically, as the white light filter 14a does, the barrier filter 24 has transmittance properties that allow light in the wavelength band of 400 to 740 nm as represented by the correlation line C1 shown in FIG. 3. When the excitation light from the light source device 10 is applied to the observed region 100, the barrier filter 24 with such transmittance properties cuts off the excitation light that is reflected from the observed region 100 out of the light that is concentrated by the objective lens 23, and allows the fluorescent light from the observed region 100 to pass to the imaging unit 25. When the white light from the light source device 10 is applied to the observed region 100, the barrier filter 24 allows the reflected light from the observed region 100 that is concentrated by the objective lens 23, i.e., the white light of 400 to 740 nm that is reflected from the observed region 100, to pass to the imaging unit 25.

The imaging unit 25 captures the reflected light image of the observed region 100 based on the illuminating light that is reflected from the observed region 100 due to application of the illuminating light and the fluorescent light image of the observed region 100 based on the fluorescent light that is generated from the observed region 100 due to application of the excitation light. Specifically, the imaging unit 25 includes an imaging device 25a, such as a CCD or a CMOS image sensor; and a movable optical system 25b, such as a lens that forms an optical image of a subject on a light receiver of the imaging device 25a. Under the control of the controller 39 of the image processing device 30 to be described below, the imaging unit 25 captures the reflected light image and the fluorescent light image of the observed region 100 while adjusting its focus.

The imaging device 25a is a Bayer color imaging device that includes a group of color filters with different spectral properties arranged on the light receiver. The imaging device 25a receives the light from the observed region 100 that is imaged by the movable optical system 25b via the color filter group, and performs a photoelectric conversion process on the received light with respect to each pixel of each color component in order to generate video signals of the observed region 100. When the white light from the light source device 10 is applied to the observed region 100, the imaging device 25a receives the white light from the observed region 100 that is imaged by the movable optical system 25b via the color filter group, thereby capturing the white light image, which is an example of the reflected light image of the observed region 100. Each time the imaging device 25a captures a white light image of the observed region 100, the imaging device 25a sequentially transmits video signals of each color component constituting the white light image of the observed region 100 to the image processing device 30.

The imaging device 25a has a function of capturing the fluorescent light image based on the fluorescent light from the subject. In other words, when the excitation light from the light source device 10 is applied to the observed region 100, the imaging device 25a receives the fluorescent light from the observed region 100 that is imaged by the movable optical system 25b via the color filter group, thereby capturing the fluorescent light image of the observed region 100. Each time the imaging device 25a captures a fluorescent light image of the observed region 100 as described above, the imaging device 25a sequentially transmits each video signal of the fluorescent light image of the observed region 100 to the image processing device 30.

The color filter group arranged on the light receiver of the imaging device 25a consists of a plurality of color filters with different spectral properties, for example, a mosaic primary color filter that includes a plurality of blue light color filters that allow blue light to pass, a plurality of a green light color filters that allow green light to pass, and a plurality of red light color filters that allow red light to pass. The color filter group separates the white light or the fluorescent light from the observed region 100 with the color filters of the respective color components with respect to each pixel of the imaging device 25a and allows the separated light of each color component to pass to each pixel of the imaging device 25a. The color components of the respective color filters contained in the color filter group are not limited to blue, green, and red, and they may be, for example, yellow, cyan, and magenta.

The movable optical system 25b is configured with an optical system, such as a lens, and a movable lens frame. The movable optical system 25b is driven and controlled by the controller 39 of the image processing device 30. Specifically, the movable optical system 25b is driven under the control of the controller 39, so that the relative distance between the imaging device 25a and the lens can be changed. The focus of the movable optical system 25b is controlled by the controller 39, and thus the movable optical system 25b focuses on the observed region 100. With the focus being on the observed region 100, the movable optical system 25b images the white light or the fluorescent light from the observed region 100, which passes through the barrier filter 24, on the light receiver of the imaging device 25a. In this case, the imaging device 25a captures the white light image or the fluorescent light image of the observed region 100 that is being focused on.

The movable optical system 25b can shift the focus from the observed region 100 at a desired degree under the control of the controller 39. With the focus being shifted from the observed region 100 under the control of the controller 39, the movable optical system 25b images the white light from the observed region 100, which passes through the barrier filter 24, on the light receiver of the imaging device 25a. In this case, after the focus is controlled, the imaging device 25a captures a focus-controlled white light image of the observed region 100 after the focus control (hereinafter, "adjusted image"). Thereafter, the movable optical system 25b returns to the state where it focuses on the observed region 100 under the control of the controller 39. The adjusted image of the observed region 100 is one of a white light image based on white light from the observed region 100, and the gradation level of the adjusted image varies depending on the result of adjusting the focus of the movable optical system 25b under the control of the controller 39.

The image processing device 30 processes the information of the images of the observed region 100 that is captured by the imaging device 26, and outputs the white light image and the fluorescent light image of the observed region 100. Specifically, as represented in FIG. 1, the image processing device 30 includes an image acquiring unit 31 that acquires the information of the images of the observed region 100, which are captured by the imaging unit 25 of the imaging system 26; and a storage unit 32 that stores the image information of the observed region 100 that is acquired by the image acquiring unit 31. The image processing device 30 includes a feature value calculator 33 that calculates a feature value of the reflected light image of the observed region 100; and a gradation level setting unit 34 that sets the gradation level of the reflected light image of the observed region 100. The image processing device 30 further includes a corrected fluorescent light image generator 35 that generates a corrected fluorescent light image that is obtained by correcting the luminance value of the fluorescent light image of the observed region 100; a white light image generator 36 that generates the white light image of the observed region 100; an image output unit 37 that outputs the white light image and the fluorescent light image of the observed region 100; an input unit 38; and the controller 39.

In the image processing device 30, the image acquiring unit 31 is connected to the imaging unit 25, the storage unit 32, the feature value calculator 33, and the corrected fluorescent light image generator 35. The storage unit 32 is connected to the corrected fluorescent light image generator 35 and the white light image generator 36. The feature value calculator 33 is connected to the gradation level setting unit 34. The corrected fluorescent light image generator 35 and the white light image generator 36 are connected to the image output unit 37. The controller 39 has bidirectional connection with the image acquiring unit 31, the feature value calculator 33; the gradation level setting unit 34, the corrected fluorescent light image generator 35, the white light image generator 36, the image output unit 37, and the input unit 38. The controller 39 also has bidirectional direction with the light source device 10 and the imaging unit 25.

The image acquiring unit 31 acquires the information of the images of the observed region 100 that are captured by the imaging system 26. Specifically, each time the imaging unit 25 captures a white light image of the observed region 100 with the focus being on the observed region 100, the image acquiring unit 31 acquires each video signal of the white light image of the observed region 100 from the imaging unit 25. Each video signal of the white light image is an analog signal and is sequentially output from the imaging unit 25 to the image acquiring unit 31 at a predetermined time interval. The image acquiring unit 31 converts each video signal of the white light image, which is acquired from the imaging unit 25, from an analog signal to a digital signal and performs signal processes, such as a noise reduction process, on each video signal after the digital conversion. The image acquiring unit 31 sequentially transmits each video signal of the white light image after the signal processes to the storage unit 32 and the feature value calculator 33.

Each time the imaging unit 25 captures a fluorescent light image of the observed region 100 with the focus being on the observed region 100, the image acquiring unit 31 acquires each video signal of the fluorescent light image of the observed region 100 from the imaging unit 25. Each video signal of the fluorescent light image is an analog signal and is sequentially output from the imaging unit 25 to the image acquiring unit 31 at a predetermined time interval. The image acquiring unit 31 converts each video signal of the fluorescent light image that is acquired from the imaging unit 25 from an analog signal to a digital signal, and performs the signal processes, such as the noise reduction process, on each video signal after the digital conversion. The image acquiring unit 31 sequentially transmits each video signal of the fluorescent light image after the signal processes to the storage unit 32.

After the controller 39 controls the focus of the imaging system 26, the image acquiring unit 31 also acquires information of an image of the observed region 100 with the shifted focus. Specifically, each time the imaging unit 25 captures a white light image of the observed region 100 with the focus being shifted from the observed region 100 under the control of the controller 39, the image acquiring unit 31 acquires each video signal of the adjusted image of the observed region 100 that is the focus-controlled white light image from the imaging unit 25. As in the above case of the white light image, each video signal of the adjusted image is sequentially output at a predetermined time interval from the imaging unit 25 to the image acquiring unit 31, and then is converted to a digital signal by the image acquiring unit 31. The image acquiring unit 31 performs the signal processes, such as the noise reduction process, on each video image signal of the adjusted image after the digital conversion, and sequentially transmits each video signal of the adjusted image after the signal processes to the corrected fluorescent light image generator 35.

The storage unit 32 stores the image information that is acquired by the image acquiring unit 31. Specifically, the storage unit 32 sequentially acquires each video signal of the white light image of the observed region 100, which is processed by the image acquiring unit 31, and then stores each acquired video signal of the white light image. The storage unit 32 also sequentially acquires each video signal of the fluorescent light image of the observed region 100, which is processed by the image acquiring unit 31, and stores each acquired video signal of the fluorescent light image. Each time the storage unit 32 acquires image information from the image acquiring unit 31, the storage unit 32 sequentially updates the existing image information to the acquired image information. The white light image and the fluorescent light image of the observed region 100 that are stored in the storage unit 32 are information of the images that are acquired with the focus being the observed region 100. Each video signal of the white light image in the storage unit 32 is appropriately read by the white light image generator 36. Each video signal of the fluorescent light image in the storage unit 32 is appropriately read by the corrected fluorescent light image generator 35.

The feature value calculator 33 calculates the feature value of the reflected light image of the observed region 100, which is acquired by the image acquiring unit 31. Specifically, the feature value calculator 33 is configured with, for example, a Laplacian filter. The feature value calculator 33 acquires each video signal of the white light image of the observed region 100 from the image acquiring unit 31 and detects the edge that is contained in the white light image on the basis of each acquired video signal. The edge in the white light image is a luminance boundary region in the image. Specifically, the edge is a pixel region where the difference in luminance with respect to the neighboring pixels is large in accordance with an image of a line object, for example, vessels contained in the white light image. The feature value calculator 33 performs an edge detection process for detecting the entire edge contained in the white light image of the observed region 100, using the Laplacian filter. The feature value calculator 33 calculates edge information that is an example of the feature value of the white light image on the basis of the white light image after the edge detection process. The edge information of the white light image, which is calculated by the feature value calculator 33, is information on the edge in the white light image. The edge information is, for example, the total luminance value of the entire edge that is contained in the white light image. The feature value calculator 33 transmits the edge information that is calculated as the feature value of the white light image of the observed region 100 to the gradation level setting unit 34.

The feature value calculator 33 performs the edge detection process using the Laplacian filter. However, the filter used for the edge detection process is not limited to the Laplacian filter. In other words, the feature value calculator 33 may detects the edge in the white light image of the observed region 100 using methods other than the Laplacian filter process.

The gradation level setting unit 34 sets the gradation level of the reflected light image of the observed region 100. Specifically, the gradation level setting unit 34 includes a data table 34a, such as a lookup table, used for setting the gradation level of the reflected light image. The data table 34a contains each range of edge information of the white light image of the observed region 100, which edge information is an example of the feature value of the reflected light image, and contains gradation levels that are different depending on the ranges. Each gradation level in the data table 34a increases with a shift of the range to an increase of the edge information, and it decreases with a shift of the range to a decrease of the edge information. The gradation level setting unit 34 acquires the edge information of the white light image of the observed region 100 from the feature value calculator 33, and selects a gradation level that corresponds to the acquired edge information with reference to the data table 34a. The gradation level setting unit 34 sets the selected gradation level as the gradation level of the white light image of the observed region 100. In this case, the gradation level setting unit 34 increases the gradation level of the white light image with an increase of the edge information, which is acquired from the feature value calculator 33, and reduces the gradation level of the white light image with a decrease of the edge information, which is acquired from the feature value calculator 33. The gradation level setting unit 34 transmits the result of setting the gradation level to the controller 39.

The data table 34a of the gradation level setting unit 34 may be previously stored in the gradation level setting unit 34. Alternatively, the data table 34a may be input by the input unit 38 or may be saved or updated in the gradation level setting unit 34 under the control of the controller 39.

The corrected fluorescent light image generator 35 generates the corrected fluorescent light image that is obtained by correcting the luminance value of the fluorescent light image of the observed region 100 that is captured by the imaging unit 25. Specifically, the corrected fluorescent light image generator 35 reads each video signal of the fluorescent light image of the observed region 100 from the storage unit 32. The corrected fluorescent light image generator 35 performs signal processes, such as an interpolation process and a white balance process, on the read fluorescent light image with respect to each video signal in order to generate the fluorescent light image of the observed region 100 is generated. The corrected fluorescent light image generator 35 also acquires each video signal of the adjusted image of the observed region 100 from the image acquiring unit 31. The corrected fluorescent light image generator 35 performs the signal processes, such as the interpolation process and the white light balance process, on each video signal of the acquired adjusted image, thereby generating the adjusted image of the observed region 100.

The adjusted image of the observed region 100 is the white light image with gradation in accordance with the gradation level that is set by the gradation level setting unit 34, i.e., the white light image with the reduced edge corresponding to the image of the line object that is originally contained in the white light image. The adjusted image is close to a uniform image without edge. The corrected fluorescent light image generator 35 performs division regarding the fluorescent light image of the observed region 100 using the adjusted image close to the uniform image in order to generate the corrected fluorescent light image of the observed region 100. In this case, the corrected fluorescent light image generator 35 divides the luminance value of the fluorescent light image to be corrected by the luminance value of the adjusted image with respect to each corresponding pixel between the adjusted image and the fluorescent light image of the observed region 100. Accordingly, the luminance value of each pixel of the fluorescent light image to be corrected is normalized. The normalization process allows the corrected fluorescent light image generator 35 to accurately correct the brightness and darkness (the luminance value) in the fluorescent light image that vary depending on the imaging distance between the observed region 100, which is the object, and the imaging system 26 (for example, the imaging unit 25) without influence of the line object that is contained in the object. The corrected fluorescent light image generator 35 sequentially transmits each video signal of the corrected fluorescent light image of the observed region 100, which is generated as described above, to the image output unit 37.

In the corrected fluorescent light image of the observed region 100 that is generated by the corrected fluorescent light image generator 35, the lesion 101 from which the fluorescent light is generated due to application of the excitation light is drawn in pixels with relatively high luminance regardless of the imaging distance between the observed region 100 and the imaging system 26.

The white light image generator 36 generates the white light image of the observed region 100 that is captured by the imaging unit 25. Specifically, the white light image generator 36 reads video signals of each color component of the white light image of the observed region 100 from the storage unit 32. The white light image generator 36 performs the interpolation process on the read video signals of each color component in order to generate a 3-CCD video signal that is obtained by combining the color components with respect to each pixel-unit assembly in the light receiver of the imaging unit 25. The white light image generator 36 performs a color conversion process and the gradation conversion process on each 3-CCD video signal, which is generated as described above, in order to generate the white light image of the observed region 100. The white light image generator 36 sequentially transmits each video signal of the generated white light image of the observed region 100 to the image output unit 37.

The image output unit 37 outputs the white light image and the corrected fluorescent light image of the observed region 100. Specifically, the image output unit 37 is configured with a desired display, such as a CRT display or a liquid crystal display. The image output unit 37 acquires each video signal of the corrected fluorescent light image of the observed region 100 from the corrected fluorescent light image generator 35 and acquires each video signal of the white light image of the observed region 100 from the white light image generator 36. The image output unit 37 displays and outputs the corrected fluorescent light image of the observed region 100 on the basis of each video signal that is acquired from the corrected fluorescent light image generator 35, and displays and outputs the white light image of the observed region 100 on the basis of each video signal that is acquired from the white light image generator 36. In this case, the image output unit 37 may display the white light image and the corrected fluorescent light image of the observed region 100 side by side, or may display them such that the corrected fluorescent light image is superimposed on the white light image of the observed region 100.

The input unit 38 functions as an external interface unit of the image processing device 30. The input unit 38 is configured with input devices, for example, a keyboard and a mouse. The input unit 38 inputs various types of information to the controller 39 in response to the input operation by the user, such as a doctor or a nurse. The various types of information that is input by the input unit 38 to the controller 39 includes, for example, instruction information for instructing the controller 39 to control the operations of the light source device 10 or of the image processing device 30, information for setting the mode in which a white light image or a fluorescent light image of the observed region 100 is captured, and information in the data table 34a that is stored in the gradation level setting unit 34.

The input unit 38 may include a power supply switch that switches on or off the power supply to the image processing device 30, may include a shutter button for starting the image capturing operation, or may include a mode switching button for switching between various modes including the image capturing mode. In this case, the controller 39 controls the operation of the light source device 10 and the operation of the imaging unit 25.

The controller 39 controls each operation of the image acquiring unit 31, the feature value calculator 33, the gradation level setting unit 34, the corrected fluorescent light image generator 35, the white light image generator 36, the image output unit 37, and the input unit 38, which are constituents of the image processing device 30, and controls input and output of signals between these constituents. The controller 39 also controls the light source device 10 and the imaging system 26.

Specifically, the controller 39 is configured with a storage unit 39a that stores predetermined process programs including an image processing program, and a computer that executes the process programs in the storage unit 39a. The storage unit 39a is a computer-readable storage medium according to the first embodiment. On the basis of setting information that is input by the input unit 38, the controller 39 sets various image-capturing conditions, such as a mode in which a white light image or a fluorescent light image of the observed region 100 is captured, or a gain. The controller 39 drives and controls the movable optical system 25b of the imaging unit 25 such that it focuses on the observed region 100, and controls the imaging device 25a such that it captures the white light image and the fluorescent light image of the observed region 100 in this focused state. The controller 39 also captures the gradation level that is set by the gradation level setting unit 34, drives and controls the movable optical system 25b on the basis of the acquired gradation level in order to control the focus of the imaging unit 25 such that the focus is shifted from the observed region 100 by an amount of shift in accordance with the gradation level. The controller 39 controls the imaging device 25a such that it captures the adjusted image of the observed region 100 in the unfocused state. Thereafter, the controller 39 drives and controls the movable optical system 25b such that it returns to the state where it focuses on the observed region 100.

The controller 39 controls the start of operation, completion of operation, and operation timing of each constituent of the image processing device 30 on the basis of instruction information that is input by the input unit 38. Specifically, the controller 39 controls the image acquiring unit 31 such that it sequentially outputs each video signal of the white light image, which is captured by the imaging unit 25, to the storage unit 32 and the feature value calculator 33 after converting each video signal to a digital signal, and such that it sequentially outputs each video signal of the adjusted image, which is captured by the imaging unit 25, to the corrected fluorescent light image generator 35 after converting each video signal to a digital signal. The controller 39 further controls the image acquiring unit 31 such that it sequentially outputs each video signal of the fluorescent light image, which is captured by the imaging unit 25, to the storage unit 32 after converting each video signal to a digital signal. The controller 39 also controls the process for calculating the feature value of the white light image that is performed by the feature value calculator 33, the process for setting the gradation level of the white light image that is performed by the gradation level setting unit 34, the process for generating the corrected fluorescent light image that is performed by the corrected fluorescent light image generator 35, and the process for generating the white light image that is performed by the white light image generator 36. The controller 39 also controls the image output unit 37 such that it displays and outputs the corrected fluorescent light image of the observed region 100, which is generated by the corrected fluorescent light image generator 35, and the white light image of the observed region 100, which is generated by the white light image generator 36.

The controller 39 controls the light emitting operation of the white light source 11 of the light source device 10 and the filter switching operation of the rotation filter 14 on the basis of the instruction information that is input by the input unit 38. Specifically, the controller 39 causes the white light source 11 to emit white light and controls driving of the motor 15 to rotate that is connected to the rotation filter 14 via the rotation shaft, thereby controlling driving of the rotation filter 14 to rotate. The controller 39 thus causes the white light filter 14a and the excitation light filter 14b to be positioned alternately in the optical path of the white light from the white light source 11 at a predetermined time interval. In this manner, the controller 39 controls switching of the rotation filter 14 in the optical path. In addition, the controller 39 knows which of the white light filter 14a and the excitation light filter 14b is positioned in the optical path on the basis of the rotation drive state, such as the rotational speed of the motor 15. When the white light filter 14a is positioned in the optical path, the controller 39 controls the imaging unit 25 such that is captures the white light image or the adjusted image of the observed region 100. When the excitation light filter 14b is positioned in the optical path, the controller 39 controls the imaging unit 25 such that it captures the fluorescent light image of the observed region 100.

Figure 4:
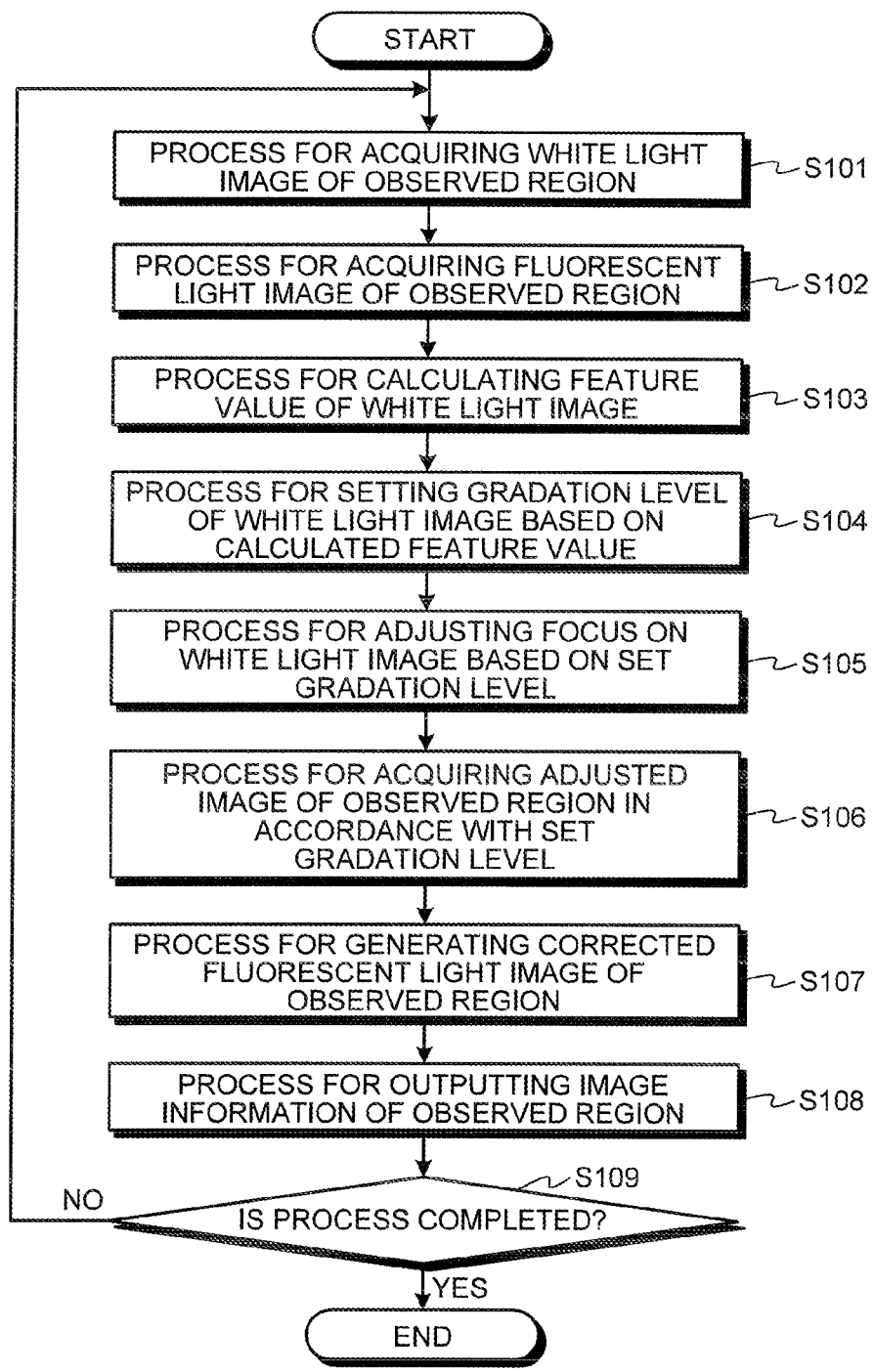
FIG. 4 is a flowchart illustrating a process procedure of an image processing device according to the first embodiment of the present invention.

The operations of the image processing device 30 according to the first embodiment of the present invention are explained below. FIG. 4 is a flowchart illustrating the process procedure of the image processing device according to the first embodiment of the present invention. The image processing device 30 according to the first embodiment performs the process procedure represented in FIG. 4 to display and output the white light image and the corrected fluorescent light image of the observed region 100.

In other words, as represented in FIG. 4, the image processing device 30 first acquires the white light image of the observed region 100 (step S101). At step S101, the controller 39 controls the light source device 10, the imaging system 26, and the image acquiring unit 31 such that the white light image of the observed region 100 that is being focused on is acquired.

Under the control of the controller 39, the light source device 10 emits the white light with the white light source 11 and positions the white light filter 14a of the rotation filter 14 in the optical path of the white light in order to apply the white light of 400 to 740 nm to the observed region 100. The imaging unit 25 of the imaging system 26 focuses on the observed region 100 because of drive and control of the movable optical system 25b by the controller 39, and receives the white light that is reflected from the observed region 100 in this focused state, thereby capturing the white light image of the observed region 100. Under the control of the controller 39, the image acquiring unit 31 acquires each video signal of the white light image of the observed region 100 from the imaging unit 25 and transmits each acquired video signal to the storage unit 32 and the feature value calculator 33 after performing the above-described signal processes. The storage unit 32 acquires each video signal of the white light image of the observed region 100, which is acquired from the image acquiring unit 31.

Subsequently, the image processing device 30 acquires the fluorescent light image of the observed region 100 to be corrected (step S102). At step S102, the controller 39 controls the light source device 10, the imaging system 26, and the image acquiring unit 31 such that the fluorescent light image of the observed region 100 that is being focused on is acquired.

Under the control of the controller 39, the light source device 10 emits the white light with the white light source 11, and positions the excitation light filter 14b of the rotation filter 14 in the optical path of the white light. Accordingly, the light source device 10 applies the excitation light with which the fluorescent light in the wavelength band of the white light can be generated to the observed region 100 (specifically, in the wavelength band of 400 to 740 nm) to the observed region 100. With the focus being on the observed region 100, the imaging unit 25 of the imaging system 26 captures the fluorescent light image of the observed region 100 by receiving the fluorescent light that is generated from the observed region 100 due to application of the excitation light. Under the control of the controller 39, the image acquiring unit 31 acquires each video signal of the fluorescent light image of the observed region 100 from the imaging unit 25 and transmits each acquired image signal to the storage unit 32 after performing the above-descried signal processes. The storage unit 32 stores each video signal of the fluorescent light image of the observed region 100, which is acquired from the image acquiring unit 31.

The image processing device 30 performs the process for calculating the feature value of the white light image of the observed region 100 (step S103). At step S103, the controller 39 controls the feature value calculator 33 such that it calculates the feature value of the white light image of the observed region 100, which is acquired at step S101.

Under the control of the controller 39, the feature value calculator 33 detects the entire edge in the white light image of the observed region 100 on the basis of each video signal of the white light image, which is acquired from the image acquiring unit 31. On the basis of the white light image after the edge detection process, the feature value calculator 33 calculates the edge information of the white light image, for example, the total luminance value of the entire edge in the white light image. The feature value calculator 33 transmits the calculated edge information of the white light image of the observed region 100 to the gradation level setting unit 34.

Subsequently, the image processing device 30 performs the process for setting the gradation level of the white light image of the observed region 100 on the basis of the feature value that is calculated at step S103 (step S104). At step S104, the controller 39 controls the gradation level setting unit 34 such that it sets the gradation level of the white light image of the observed region 100 on the basis of the feature value that is calculated at step S103.

Under the control of the controller 39, the gradation level setting unit 34 acquires the edge information, which is calculated at step S103 by the feature value calculator 33, and sets the gradation level of the white light image of the observed region 100 in accordance with the acquired edge information with reference to the data table 34*a*. The gradation level setting unit 34 transmits the set gradation level of the white light image of the observed region 100 to the controller 39.

Subsequently, the image processing device 30 performs the process for adjusting the focus of the white light image of the observed region 100 on the basis of the gradation level that is set at step S104 (step S105). At step S105, the controller 39 acquires the gradation level of the white light image of the observed region 100, which is set by the gradation level setting unit 34, and calculates the amount of shift of the focus from the observed region 100 on the basis of the acquired gradation level. The controller 39 controls the focus of the imaging system 26 such that its focus is shifted from the observed region 100 by the calculated amount of a shift.

Under the control of the controller 39, the imaging unit 25 of the imaging system 26 changes the relative distance between the imaging device 25*a* and the lens of the movable optical system 25*b* in order to shift the focus from the observed region 100 by the amount of a shift in accordance with the gradation level that is set by the gradation level setting unit 34.

The image processing device 30 then acquires the adjusted image that is the focus-controlled white light image of the observed region 100 in accordance with the set gradation level (step S106). At step S106, the controller 39 controls the light source device 10, the imaging system 26, and the image acquiring unit 31 such that the adjusted image of the observed region 100 in the unfocused state in accordance with the set gradation level.

Under the control of the controller 39, the light source device 10 emits the white light with the white light source 11 and positions again the white light filter 14*a* of the rotation filter 14 in the optical path of the white light. Accordingly, the light source device 10 applies the white light of 400 to 740 nm to the observed region 100. The imaging unit 25 of the imaging system 26 receives the white light that is reflected from the observed region 100 with the focus being adjusted at step S105, thereby capturing the adjusted image of the observed region 100. Under the control of the controller 39, the image acquiring unit 31 acquires each video signal of the adjusted image of the observed region 100 from the imaging unit 25 and transmits each acquired video signal to the corrected fluorescent light image generator 35 after performing the above-described signal processes.

The image processing device 30 perform the process for generating the corrected fluorescent light image of the observed region 100 using the adjusted image of the observed region 100 that is acquired at step S106 (step S107). At step S107, the controller 39 controls the corrected fluorescent light image generator 35 such that it generates the corrected fluorescent light image that is obtained by correcting the luminance value of the fluorescent light image of the observed region 100, which is acquired at step S102.

Under the control of the controller 39, the corrected fluorescent light image generator 35 performs the normalization process on the fluorescent light image of the observed region 100 to be corrected, using the adjusted image of the observed region 100 that is acquired at step S106, thereby generating the corrected fluorescent light image of the observed region 100. Specifically, the corrected fluorescent light image generator 35 performs the signal processes on each video signal of the fluorescent light image of the observed region 100, which is read from the storage unit 32, thereby generating the fluorescent light image of the observed region 100. The corrected fluorescent light image generator 35 performs the signal processes on each pixel of the adjusted image of the observed region 100, which is acquired from the image acquiring unit 31, thereby generating the adjusted image of the observed region 100. The corrected fluorescent light image generator 35 divides the luminance value of the fluorescent light image to be corrected by the luminance value of the adjusted image, with respect to each corresponding pixel between the adjusted image and the fluorescent light image of the observed region 100, thereby normalizing the luminance value of each pixel of the fluorescent light image to be corrected. Accordingly, the corrected fluorescent light image generator 35 generates the corrected fluorescent light image of the observed region 100 that is obtained by correcting the luminance value of the fluorescent light image to be corrected. The corrected fluorescent light image generator 35 transmits each video signal of the generated fluorescent light image of the observed region 100 to the image output unit 37.

Subsequently, the image processing device 30 performs the process for outputting the image information of the observed region 100 (step S108). At step S108, the controller 39 controls the white light image generator 36 such that it generates the white light image of the observed region 100 and controls the image output unit 37 such that it displays the white light image and the corrected fluorescent light image of the observed region 100 to be output.

Under the control of the controller 39, the white light image generator 36 reads video signals of each color component of the white light image of the observed region 100 from the storage unit 32, and performs the above-described various signal processes on the read video signals of each color component, thereby generating the white light image of the observed region 100. The white light image generator 36 transmits each video signal of the generated white light image of the observed region 100 to the image output unit 37. Under the control of the controller 39, the image output unit 37 displays and outputs the corrected fluorescent light image of the observed region 100, which is acquired from the corrected fluorescent light image generator 35, and the white light image of the observed region 100, which is acquired from the white light image generator 36.

Thereafter, when a process completion operation, such as a predetermined off operation, is performed (YES at step S109), the image processing device 30 completes the process. In this case, the input unit 38 inputs instruction information for completing the process. On the basis of the input instruction information, the controller 39 completes the operations of the light source device 10, the imaging system 26, and each constituent of the image processing device 30. In contrast, when the process completion operation is not performed (NO at step S109), the image processing device 30 goes back to step S101 and repeats the process procedure from step S101 and the following steps. In this case, the controller 39 performs the process procedure from step S101 to step S109 in order to appropriately control the light source device 10, the imaging system 26, and each constituent of the image processing device 30.

Figure 5:
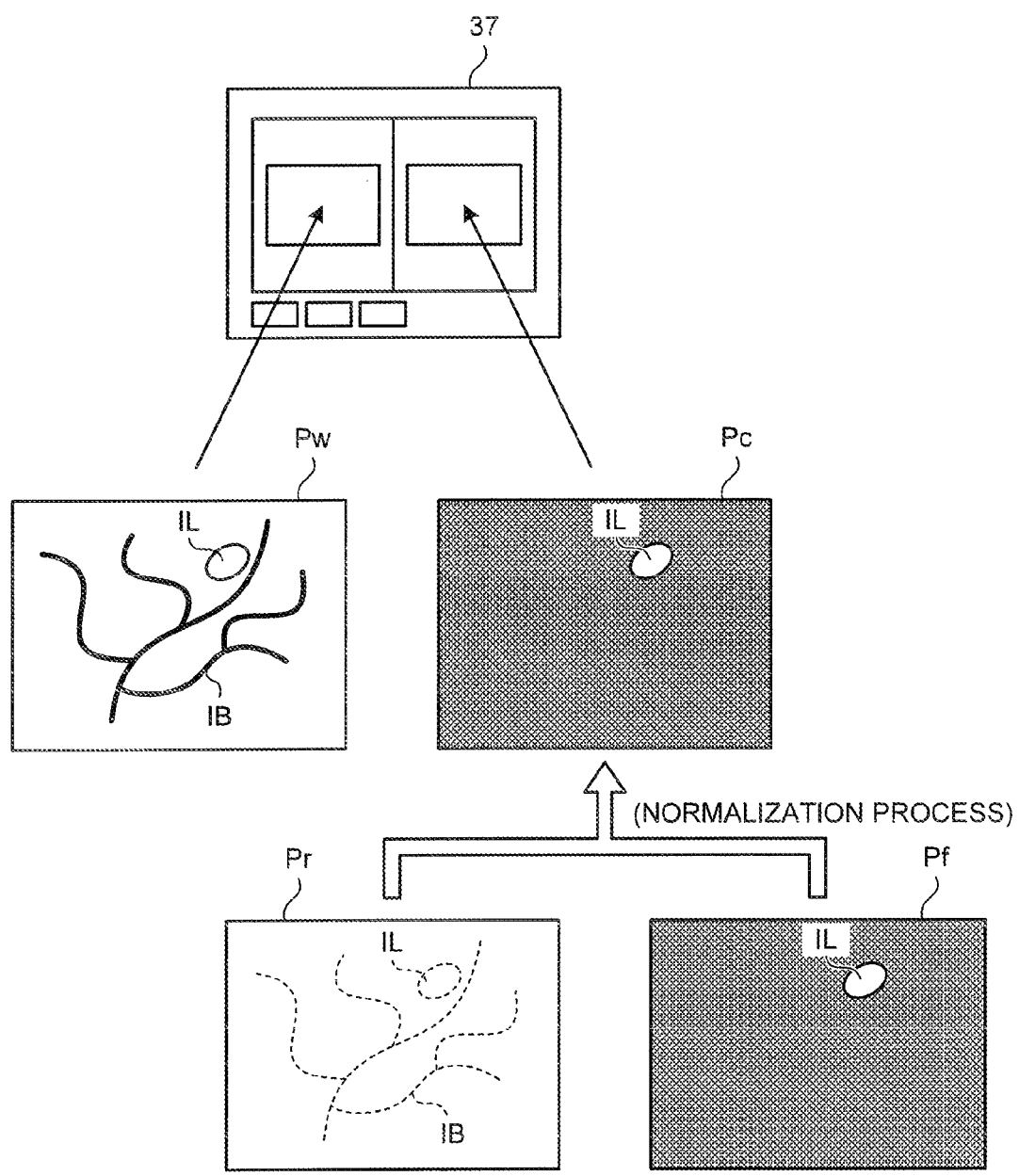
FIG. 5 is a schematic diagram for specifically explaining operations of the image processing device according to the first embodiment.

The operations of the image processing device 30 based on the process procedure from step S101 to S109 are specifically explained below, taking, as an example, a case where the image of the line object that is contained in the white light image of the observed region 100 is an image of vessels. FIG. 5 is a schematic diagram for specifically explaining the operations of the image processing device according to the first embodiment.

The image processing device 30 acquires a white light image Pw of the observed region 100 at step S101 and acquires a fluorescent light image Pf of the observed region 100 at step S102. The white light image Pw is captured with the focus being on the observed region 100. As represented in FIG. 5, the white light image Pw contains an image IL of the lesion 101 in the observed region 100 and an image IB of vessels that are the line object. In other words, the white light image Pw contains the edge that forms the luminance contrast in accordance with the image IB of the vessels. On the other hand, the fluorescent light image Pf is captured with the focus being on the observed region 100, and contains the image IL based on the fluorescent light that is generated from the lesion 101 in the observed region 100.

The image processing device 30 that acquires the white light image Pw and the fluorescent light image Pf of the observed region 100 calculates the feature value of the white light image Pw and sets the gradation level of the white light image Pw on the basis of the calculated feature value. Specifically, at step S103, the feature value calculator 33 detects the edge that is contained in the white light image Pw, i.e., the edge that is the pixel region of which luminance is largely different from that of the neighboring pixels in accordance with the image IB of the vessels, and calculates the total luminance value of the detected entire edge in the white light image Pw as the edge information. On the other hand, the gradation level setting unit 34 acquires the edge information of the white light image Pw that is calculated by the feature value calculator 33, and sets the gradation level of the white light image Pw in accordance with the edge information with reference to the data table 34a. The gradation level setting unit 34 increases the gradation level with an increase of the total luminance value of the entire edge in the white light image Pw, which total luminance value is the edge information, and reduces the gradation level with a decrease in the total luminance value of the entire edge.

After setting the gradation level of the white light image Pw as described above, the image processing device 30 acquires the adjusted image Pr that is the white light image of the observed region 100 with gradation in accordance with the gradation level. Specifically, at steps S105 and S106, the controller 39 calculates the amount of shift of the focus in accordance with the gradation level of the white light image Pw and controls the imaging unit 25 such that it shifts the focus from the observed region 100 by the calculated shift amount. Furthermore, the controller 39 controls the light source device 10 and the imaging unit 25 such that the white light image of the observed region 100 in the unfocused state is acquired. Under the control of the controller 39, the light source device 10 applies the white light to the observed region 100 and the imaging unit 25 captures the focus-controlled white light image of the observed region 100 in the unfocused state in accordance with the gradation level, i.e., captures the adjusted image Pr. The image processing device 30 acquires the adjusted image Pr of the observed region 100 that is captured by the imaging unit 25.

The image processing device 30 that acquires the adjusted image Pr of the observed region 100 then corrects the luminance value of the fluorescent light image Pf of the observed region 100 using the adjusted image Pr. Specifically, at step S107, the corrected fluorescent light image generator 35 performs the normalization process on the fluorescent light image Pf of the observed region 100 using the adjusted image Pr of the observed region 100, thereby generating a corrected fluorescent light image Pc of the observed region 100. In the normalization process, the corrected fluorescent light image generator 35 divides the luminance value of the fluorescent light image Pf by the luminance value of the adjusted image Pr, with respect to each corresponding pixel between the adjusted image Pr and the fluorescent light image Pf, thereby normalizing the luminance value of each pixel of the fluorescent light image Pf.

The adjusted image Pr of the observed region 100 is the white light image with gradation in accordance with the gradation level that is set by the gradation level setting unit 34. The adjusted image Pr has reduced luminance contrast due to the edge corresponding to the image IB of the vessels, which are the line object in the white light image Pw of the observed region 100. Accordingly, the adjusted image Pr is close to the uniform image without edge (i.e., without luminance contrast). The corrected fluorescent light image generator 35 normalizes the luminance value of each pixel of the fluorescent light image Pf using the adjusted image Pr. Accordingly, the corrected fluorescent light image generator 35 generates the corrected fluorescent light image Pc that is obtained by accurately correcting the brightness and darkness (the luminance value) in the fluorescent light image Pf that vary depending on the imaging distance between the observed region 100 and the imaging system 26 without influence of the edge (luminance contrast) corresponding to the image IB of the vessels that are the line object.

Thereafter, as represented in FIG. 5, the image processing device 30 displays the white light image Pw and the corrected fluorescent light image Pc of the observed region 100 on the image output unit 37. In the corrected fluorescent light image Pc that is displayed on the image output unit 37, the image IL of the lesion 101 from which the fluorescent light is generated due to application of the excitation light is drawn in pixels with relatively high luminance regardless of the imaging distance between the observed region 100 and the imaging system 26. This increases the capability of detecting the lesion 101 in the subject by fluorescence observation of the observed region 100 and increases the diagnostic capability.

As described above, in the first embodiment of the present invention, first acquired are the white light image of the observed region based on the white light, which is reflected from the observed region due to application of the white light, and the fluorescent light image of the observed region based on the fluorescent light, which is generated from the observed region due to application of the excitation light. The feature value concerning the edge of the acquired white light image is calculated. On the basis of the calculated feature value, the gradation level of the white light image is set. The focus control for shifting the focus from the observed region is performed in accordance with the set gradation level, and then the adjusted image that is the focus-controlled white light image of the observed region is acquired. Division regarding the fluorescent light image of the observed region is performed using the adjusted image in order to generate the corrected fluorescent light image that is obtained by correcting the luminance value of the fluorescent light image. Therefore, even if the white light image of the observed region contains an image of a line object, such as vessels, the luminance contrast in the white light image caused by the image of the line object can be reduced by appropriately gradating the white light image. Accordingly, the luminance value of the fluorescent light image of the observed region can be normalized using the adjusted image of the observed region that is close to the uniform image without luminance contrast caused by edge. Thus, the luminance of the fluorescent light image of the observed region can be corrected with high accuracy without influence of the line object in the observed region.

By use of the image processing device, the imaging device, the computer-readable storage medium, and the image processing method, abnormal body tissue, such as a lesion, in the observed region can be clearly drawn in the fluorescent light image. This increases the capability of detecting abnormal body tissue in the subject using the fluorescent light image to be observed and increases the diagnostic capability.

Second Embodiment

A second embodiment of the present invention is explained below. In the first embodiment, the feature value calculator 33 calculates the edge information of the white light image of the observed region 100 as the feature value of the white light image. In the second embodiment, the color distribution information of a white light image of the observed region 100 is calculated as a feature value of the white light image.

Figure 6:
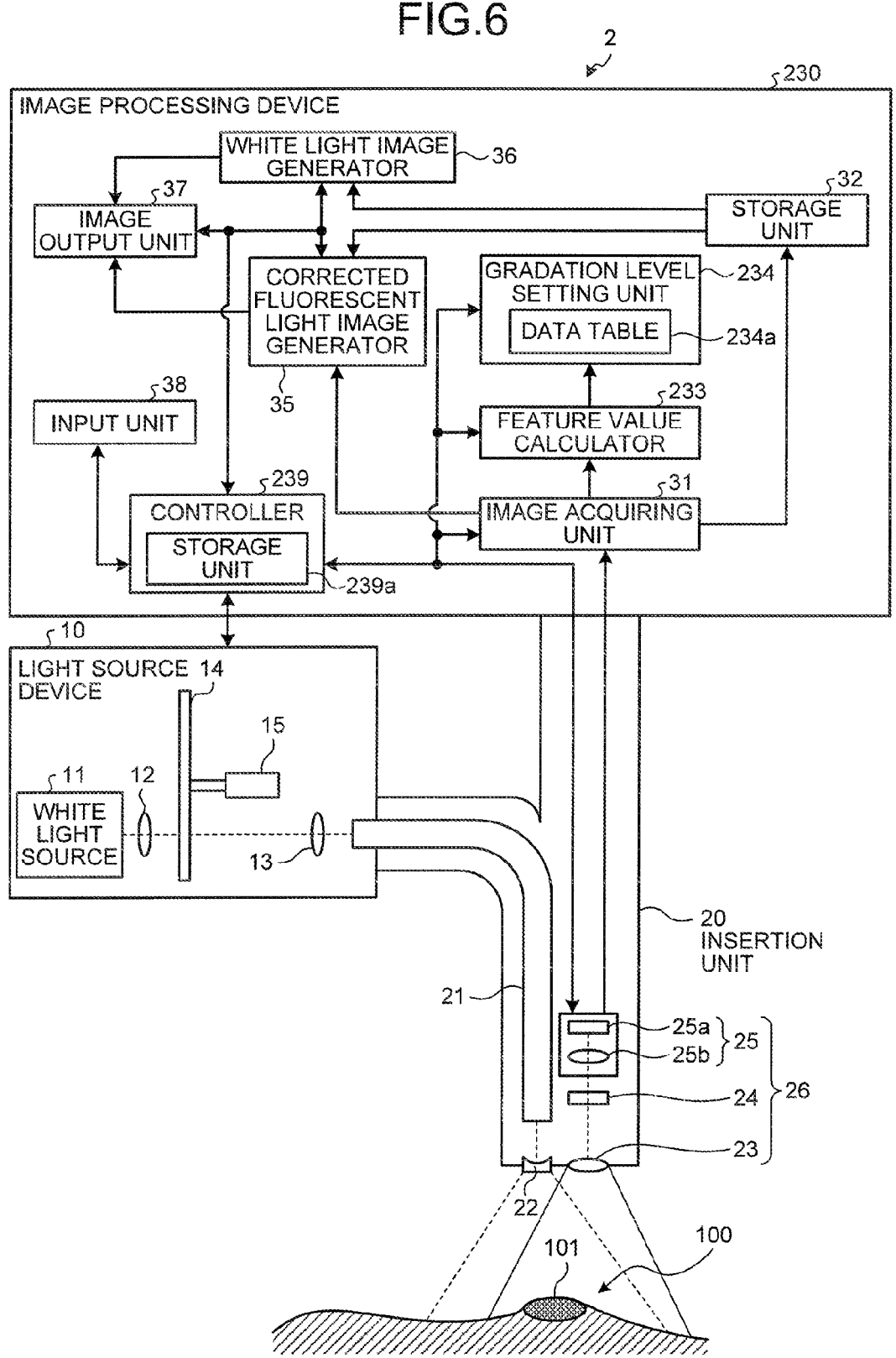
FIG. 6 is a block diagram schematically representing an example of a configuration of an endoscope according to a second embodiment of the present invention.

FIG. 6 is a block diagram schematically representing an example of a configuration of an endoscope according to the second embodiment of the present invention. As represented in FIG. 6, an endoscope 2 according to the second embodiment includes an image processing device 230 instead of the image processing device 30 according to the first embodiment. The image processing device 230 includes a feature value calculator 233 instead of the feature value calculator 33 of the image processing device 30 according to the first embodiment, a gradation level setting unit 234 instead of the gradation level setting unit 34; and a controller 239 instead of the controller 39. Other aspects of the configuration of the endoscope 2 are same as those of the first embodiment, and the same constituents are denoted by the same reference numbers.

The image processing device 230 includes the feature value calculator 233, the gradation level setting unit 234, and the controller 239 as described above. The image processing device 230 calculates the color distribution information of the white light image of the observed region 100 as the feature value of the white light image, and sets a gradation level of the white light image on the basis of the calculated color distribution information. The image processing device 230 has functions similar to those of the image processing device 30 according to the first embodiment in addition to the functions of the feature value calculator 233, the gradation level setting unit 234, and the controller 239.

The feature value calculator 233 calculates the color distribution information of the white light image of the observed region 100, which is captured by the imaging unit 25, as the feature value of the reflected light image of the observed region 100. Specifically, the feature value calculator 233 acquires each video signal of the white light image of the observed region 100 from the image acquiring unit 31 and detects a predetermined color component that is contained in the white light image on the basis of each acquired video signal. The feature value calculator 233 calculates dispersion that represents the degree of dispersion of the detected color component in the white light image. The dispersion of the predetermined color component that is calculated by the feature value calculator 233 is an example of the color distribution information as the feature value of the white light image of the observed region 100. The dispersion increases with an increase of the degree of dispersion (i.e., a decrease of the degree of concentration) of the predetermined color component in the white light image and decreases with a decrease of the dispersion degree (i.e., an increase of the concentration degree) of the predetermined color component in the white light image. The feature value calculator 233 transmits the calculated color distribution information of the white light image of the observed region 100 to the gradation level setting unit 234.

The color component of the color distribution information that is calculated by the feature value calculator 233 may be a color component that has, or contained in, the largest share among the color components that are contained in the white light image of the observed region 100, which is acquired from the image acquiring unit 31. Alternatively, the color component may be a color component of a pixel region (i.e., edge) corresponding to a line object, such as vessels, that is contained in the white light image.

The gradation level setting unit 234 includes a data table 234a instead of the data table 34a according to the first embodiment. The gradation level setting unit 234 sets the gradation level of the reflected light image of the observed region 100 with reference to the data table 234a. The data table 234a contains each range of dispersion (dispersion degree) of the predetermined color that is an example of the color distribution information of the white light image of the observed region 100 and the gradation level that differs in each range of dispersion of the predetermined color in the white light image. Each gradation level in the data table 234a decreases with a shift of the range to an increase of the dispersion of the predetermined color in the white light image, and it increases with a shift of the range to a decrease of the dispersion of the predetermined color in the white light image. The gradation level setting unit 234 acquires the color distribution information of the white light image of the observed region 100 from the feature value calculator 233, and selects a gradation level that corresponds to the acquired color distribution information with reference to the data table 234a. The gradation level setting unit 234 sets the selected gradation level as the gradation level of the white light image of the observed region 100. In this case, the gradation level setting unit 234 increases the gradation level of the white light image of the observed region 100 with a decrease of the color distribution information, which is acquired from the feature value calculator 233, i.e., a decrease of the dispersion of the predetermined color in the white light image. The gradation level setting unit 234 also reduces the gradation level of the white light image of the observed region 100 with an increase of the color distribution information, which is acquired from the feature value calculator 233, i.e., an increase of the dispersion of the predetermined color in the white light image. The gradation level setting unit 234 transmits the result of setting the gradation level to the controller 239.

The data table 234a of the gradation level setting unit 234 may be previously stored in the gradation level setting unit 234. Alternatively, the data table 234a may be input by the input unit 38 and saved or updated in the gradation level setting unit 234 under the control of the controller 239.

The controller 239 is configured with a storage unit 239a that stores predetermined process programs including an image processing program, and a computer that executes the process programs in the storage unit 239a. The storage unit 239a is a computer-readable storage medium according to the second embodiment. The controller 239 controls the feature value calculator 233 such that it calculates, as the feature value of the white light image of the observed region 100, the color distribution information of the white the white light image, for example, the dispersion of the predetermined color component in the white light image, and controls the gradation level setting unit 234 such that it sets the gradation level of the white light image using the calculated color distribution information of the white light image. The controller 239 has functions similar to those of the controller 39 of the image processing device 30 according to the first embodiment in addition to the function of controlling the feature value calculator 233 and the gradation level setting unit 234.

Figure 7A:
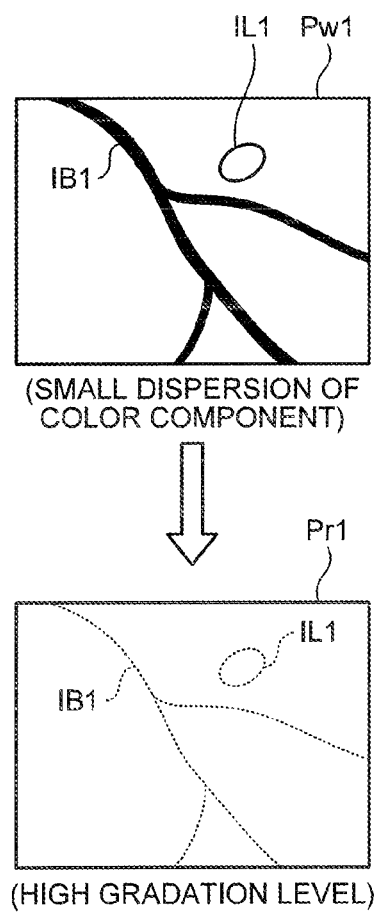
FIG. 7A is a schematic diagram specifically explaining a feature value calculation process and a gradation level setting process in a case where a white light image in which a vessel structure is relatively concentrated is captured in the second embodiment of the present invention.

The operations of the image processing device 230 according to the second embodiment of the present invention are explained below. FIG. 7A and FIG. 7B are schematic diagrams specifically explaining respectively a feature value calculation process and a gradation level setting process on the white light image according to the second embodiment of the present invention. The image processing device 230 according to the second embodiment performs operations similar to those of the image processing device 30 according to the first embodiment in addition to the feature value calculation process and the gradation level setting process on the white light image of the observed region 100. In other words, the image processing device 230 performs a process procedure similar to that of the image processing device 30 according to the first embodiment in addition to the process procedure of steps S103 and S104 out of steps S101 to S109 represented in FIG. 4.

The feature value calculation process and the gradation level setting process that are performed by the image processing device 230 on the white light image of the observed region 100 are specifically explained below with reference to FIG. 7A and FIG. 7B taking, as an example, a case where the white light image of the observed region 100 is image information that consists of each pixel of the blue color component, each pixel of the green color component, and each pixel of the red color component, and where the color component of vessels (i.e., red component) that is a line object contained in the white light image is detected.

The feature value calculation process and the gradation level setting process in a case where the image processing device 230 acquires a white light image Pw1 in which the vessel structure is relatively concentrated as represented in FIG. 7A are explained below. At step S103, the feature value calculator 233 acquires each video signal of the white light image Pw1 of the observed region 100 from the image acquiring unit 31, and detects the red color component that is the color component of the vessels in the white light image Pw1 on the basis of each acquired video signal. The feature value calculator 233 calculates the degree of dispersion of the pixels of the detected red color component in the white light image Pw1 as the dispersion of the red color component in the white light image Pw1. The feature value calculator 233 transmits the dispersion of the red color component in the white light image Pw1, which is calculated as described above, to the gradation level setting unit 234.

An image IB1 of the vessels that are the line object in the white light image Pw1 exists and is relatively concentrated in the image as represented in FIG. 7A. In this case, the dispersion of the red color component, which is calculated by the feature value calculator 233, is a relatively small value in accordance with the degree of the concentration of the vessels in the white light image Pw1.

At step S104, the gradation level setting unit 234 acquires the result of calculating the dispersion of the red color component in the white light image Pw1 from the feature value calculator 233. The gradation level setting unit 234 sets the gradation level in accordance with the acquired dispersion of the red color component in the white light image Pw1 as the gradation level of the white light image Pw1 with reference to the data table 234a. The dispersion of the red color component in the white light image Pw1 is relatively small as described above, i.e., the degree of concentration of the red color component in the white light image Pw1 is relatively large. In this case, the gradation level setting unit 234 sets relatively higher the gradation level of the white light image Pw1 in accordance with the small the small dispersion of the red color component in the white light image Pw1. Accordingly, at step S106, the image processing device 230 acquires an adjusted image Pr1 of the observed region 100 with the focus being shifted in accordance with the gradation level of the white light image Pw1.

The adjusted image Pr1 of the observed region 100 is a white light image that is gradated in a large extent in accordance with the gradation level (high) of the white light image Pw1, i.e., the image IB1 of the vessels that are the line object contained in the image is sufficiently gradated. This reduces the entire edge corresponding to the vessels in the adjusted image Pr1, and accordingly, sufficiently reduces the contrast in the adjusted image Pr1 resulting from the edge corresponding to the image IB1 of the vessels, so that the adjusted image Pr1 is close to the uniform image without contrast due to edge. As in the case of the first embodiment, the corrected fluorescent light image generator 35 of the image processing device 230 generates the corrected fluorescent light image of the observed region 100 by performing the normalization process on the fluorescent light image of the observed region 100 using the adjusted image Pr1. In the corrected fluorescent light image, an image IL1 of the lesion from which the fluorescent light is generated is drawn in pixels with relatively high luminance.

The feature calculation process and the gradation level setting process in a case where the image processing device 230 acquires a white light image Pw2 in which the vessel structure is relatively dispersed as represented in FIG. 7B are explained below. At step S103, the feature value calculator 233 acquires each video signal of the white light image Pw2 of the observed region 100 from the image acquiring unit 31, and detects the red color component that is the color component of the vessels in the white light image Pw2 on the basis of each acquired video signal. The feature value calculator 233 calculates the degree of dispersion of the pixels of the detected red color component in the white light image Pw2 as the dispersion of the red color component in the white light image Pw2. The feature value calculator 233 transmits the dispersion of the red color component in the white light image Pw2, which is calculated as described above, to the gradation level setting unit 234.

An image IB2 of the vessels that are the line object in the white light image Pw2 exists and dispersed in the relatively-entire image as represented in FIG. 7B. In this case, the dispersion of the red color component, which is calculated by the feature value calculator 233, is a relatively large value, compared to that of the white light image Pw1, in accordance with the degree of dispersion of the vessels in the white light image Pw2.

At step S104, the gradation level setting unit 234 acquires the result of calculating the dispersion of the red color component in the white light image Pw2 from the feature value calculator 233. The gradation level setting unit 234 sets the gradation level in accordance with the acquired dispersion of the red color component in the white light image Pw2 as the gradation level of the white light image Pw2 with reference to the data table 234a. The dispersion of the red color component in the white light image Pw2 is relatively large as described above (e.g., larger than that of the white light image Pw1), i.e., the degree of concentration of the red color component in the white light image Pw2 is relatively small. In this case, the gradation level setting unit 234 sets relatively lower the gradation level of the white light image Pw2 (lower than that of the white light image Pw1) in accordance with the large dispersion of the red color component in the white light image Pw2. Accordingly, at step S106, the image processing device 230 acquires an adjusted image Pr2 of the observed region 100 with the focus being shifted in accordance with the gradation level of the white light image Pw2.

The adjusted image Pr of the observed region 100 is a white light image that is gradated in a small extent in accordance with the gradation level (low) of the white light image Pw2, i.e., the image IB2 of the vessels that are the line object contained in the image is appropriately gradated. This sufficiently reduces the edge corresponding to the vessels in the adjusted image Pr, and accordingly, sufficiently reduces the contrast in the adjusted image Pr resulting from the edge corresponding to the image IB2 of the vessels, so that the adjusted image Pr is close to the uniform image without contrast due to edge. As in the case of the first embodiment, the corrected fluorescent light image generator 35 of the image processing device 230 generates the corrected fluorescent light image of the observed region 100 by performing the normalization process on the fluorescent light image of the observed region 100 using the adjusted image Pr. In the corrected fluorescent light image, an image IL2 of the lesion from which the fluorescent light is generated is drawn in pixels with relatively high luminance.

As explained above, in the second embodiment of the present invention, the feature value concerning the acquired color distribution of the white light image of the observed region is calculated. On the basis of the calculated feature value, the gradation level of the white light image is set. Other aspects of the configuration are similar to those of the first embodiment. Thus, functions and effects similar to those of the first embodiment are achieved. Particularly, the corrected fluorescent light image that is preferable to fluorescence observation of the human body with a complicated vessel structure as an line object can be generated and output.

Third Embodiment

A third embodiment of the present invention is explained below. In the first embodiment, the fluorescent light image and the adjusted image of the observed region 100 are captured at different timing. In the third embodiment, the fluorescent light image and the adjusted image of the observed region 100 are captured at the same timing.

Figure 8:
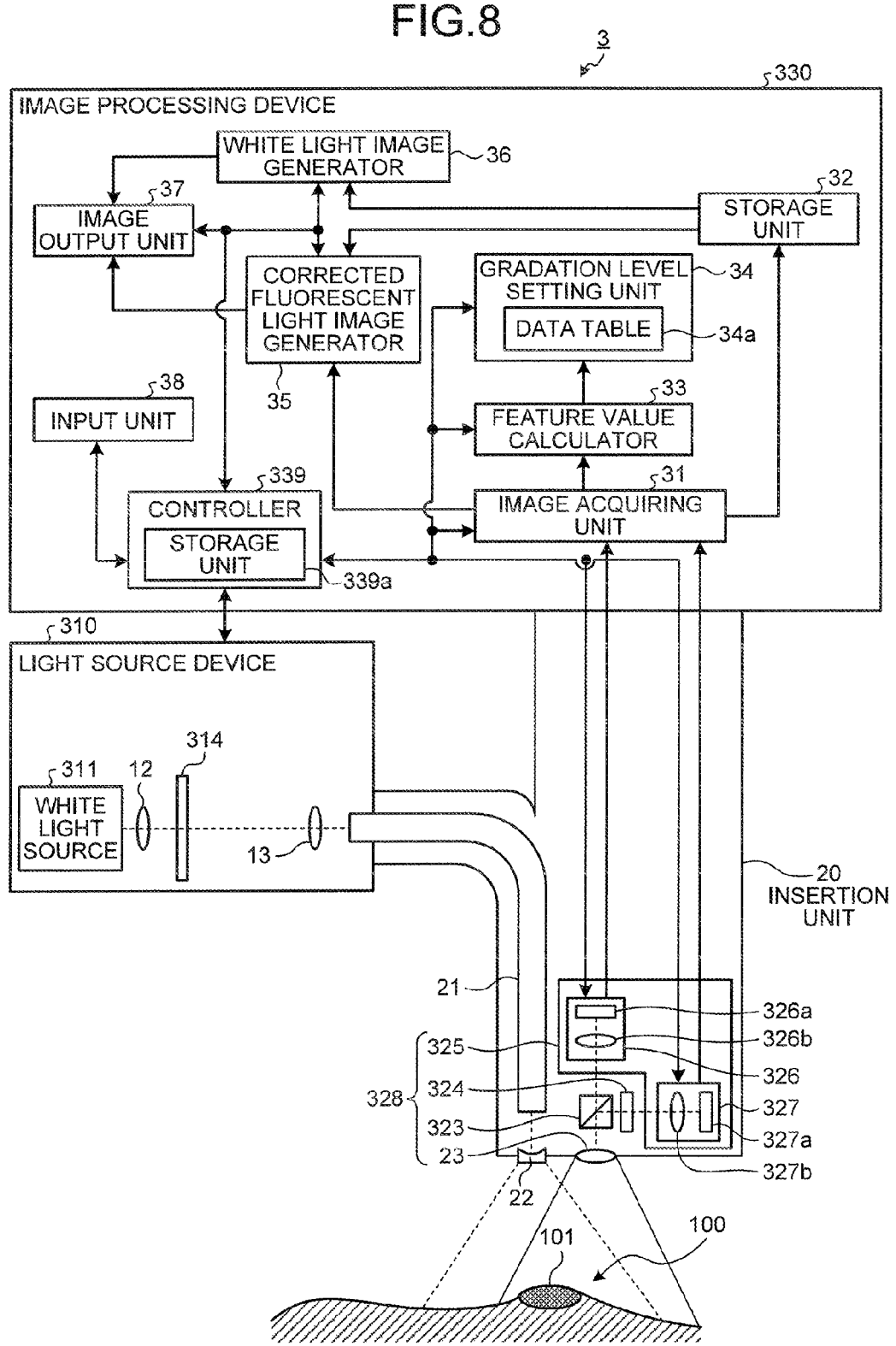
FIG. 8 is a block diagram schematically representing an example of a configuration of an endoscope according to a third embodiment of the present invention.

FIG. 8 is a block diagram schematically representing an example of a configuration of an endoscope according to the third embodiment of the present invention. As represented in FIG. 8, an endoscope 3 according to the third embodiment includes a light source device 310 instead of the light source device 10 according to the first embodiment, an imaging system 328 instead of the imaging system 26; and an image processing device 330 instead of the image processing device 30. In the third embodiment, the light source device 310 includes a white light source 311 instead of the white light source 11 of the light source device 10 according to the first embodiment; and a fixed filter 314 instead of the rotation filter 14 and the motor 15. The imaging system 328 includes a barrier filter 324 instead of the barrier filter 24 of the imaging system 26 according to the first embodiment; and a combined imaging unit 325 instead of the single imaging unit 25, and further includes a light separator that separates the light from the observed region 100. The image processing device 330 includes a controller 339 instead of the controller 39 of the image processing device 30 according to the first embodiment. Other aspects of the configuration of the endoscope 3 are same as those of the first embodiment. The same constituents are denoted by the same reference numbers.

The light source device 310 functions as a light source unit that applies excitation light for exciting a fluorescent agent and white light, which is an example of illuminating light that illuminates an object, to the observed region 100. Specifically, the light source device 310 includes the collimating lens 12; the condenser lens 13; the white light source 311 that can emit white light in a broadband covering a predetermined wavelength band of excitation light; and the filter 314 that allows light in a predetermined wavelength to pass. The light source device 310 has a function of simultaneously applying the excitation light and the white light to the observed region 100.

The white light source 311 is achieved with a light source that can emit the white light in the broadband covering the wavelength band of the excitation light that excites the fluorescent agent. The power supply to the white light source 311 is turned on or off by operating the switch (not shown) of the light source device 310 and the light emitting timing is controlled by the controller 339 of the image processing device 330. The white light source 311 emits the broadband white light in the wavelength band, for example, of 400 to 740 nm. The white light emitted by the white light source 311 contains color lights of the blue color component (B), the green color component (G), and the red color component (R), and further contains the excitation light in a wavelength band of 680 to 740 nm that excites the fluorescent agent, for example, Cy7, accumulated on the lesion 101, such as a tumor. The excitation light from the white light source 311 has a feature of exciting the fluorescent agent accumulated on the lesion 101 in order to cause emission of fluorescent light in a wavelength band, for example, of 760 to 850 nm out of the wavelength band of visible light.

Figure 9:
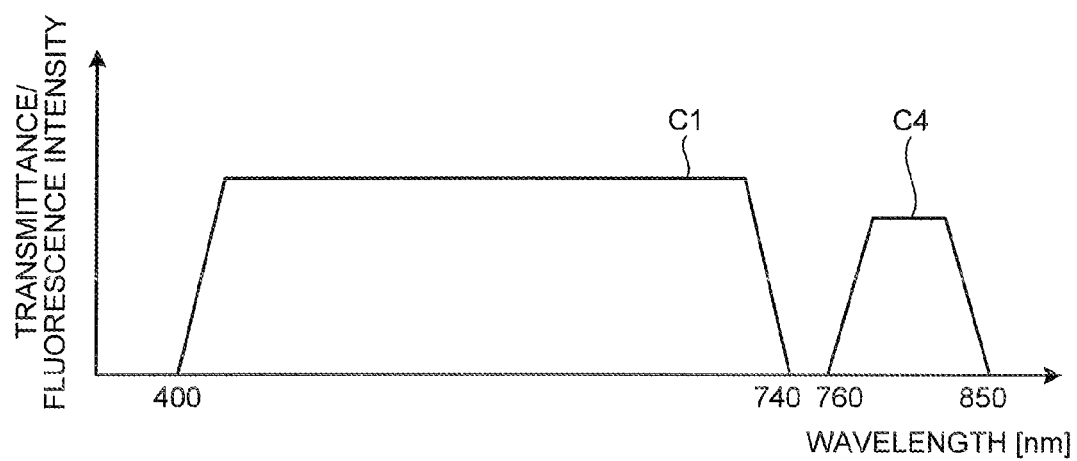
FIG. 9 is a schematic diagram representing an example of transmittance properties of a filter of a light source device according to the third embodiment of the present invention.

The filter 314 extracts light in the predetermined wavelength band from the white light that is emitted by the white light source 311. FIG. 9 is a schematic diagram representing an example of transmittance properties of the filter of the light source device according to the third embodiment of the present invention. FIG. 9 also illustrates the intensity properties of the fluorescent light that is generated due to the excitation light that is extracted by the filter 314 of the light source device 310. The filter 314 has transmittance properties that allow the white light in the wavelength band of 400 to 740 nm to pass as represented by the correlation line C1 of wavelength with respect to transmittance represented in FIG. 9. The filter 314 extracts the white light in the wavelength band of 400 to 740 nm from the light emitted by the white light source 311 and allows the extracted white light to pass as the illuminating light to the observed region 100.

The white light that is extracted by the filter 314 contains the excitation light in the wavelength band of 680 to 740 nm, which excites the fluorescent agent (for example, Cy7) accumulated on the lesion 101 in the observed region 100. In other words, the filter 314 allows the white light in the broadband covering the wavelength band of the excitation light to pass. The excitation light in the wavelength band of 680 to 740 nm that passes through the filter 314 causes generation of the fluorescent light in the wavelength band of 760 to 850 nm as represented by the correlation line C4 of wavelength with respect to intensity represented in FIG. 9. The white light and the excitation light that are emitted by the light source device 310 with such a configuration are applied simultaneously to the observed region 100 via the light guide fiber 21 of the insertion unit 20.

In the third embodiment, the insertion unit 20 includes the light guide fiber 21 and the lens 22, and further includes the imaging system 328 that captures the reflected light image and the fluorescent light image of the observed region 100. The imaging system 328 includes the objective lens 23, a light separator 323, the barrier filter 324, and the combined imaging unit 325. The combined imaging unit 325 includes a white light imaging unit 326 that captures the white light image and the adjusted image of the observed region 100; and a fluorescent light imaging unit 327 that captures the fluorescent light image of the observed region 100.

The white light from the light source device 310 that is applied to the observed region 100 via the light guide fiber 21 and the lens 22 of the insertion unit 20 illuminates the observed region 100 and is reflected on the observed region 100. Simultaneously, the excitation light that is contained in the white light is reflected on the observed region 100 and excites the fluorescent agent on the lesion 101 to cause generation of fluorescent light in a wavelength band, for example, of 760 to 850 nm. The objective lens 23 concentrates the white light and the excitation light that are reflected from the observed region 100 and the fluorescent light that is generated from the observed region 100 (specifically, the lesion 101).

The light separator 323 reflects the light from the observed region 100, which passes through the objective lens 23, to the white light imaging unit 326 and the fluorescent light imaging unit 327. Specifically, the light separator 323 is configured with a dichroic mirror or a half mirror. The light separator 323 reflects the light that contains at least the reflected white light from the observed region 100 and the light that contains at least the fluorescent light from the observed region 100, out of the light from the observed region 100 that is concentrated by the objective lens 23, respectively to the optical path of the white light imaging unit 326 and to the optical path of the fluorescent light imaging unit 327. For example, if the light separator 323 is a dichroic mirror, the light separator 323 reflects the white light in the wavelength band less than a predetermined wavelength band (for example, less than 680 nm) out of the light from the observed region 100 to the optical path of the white light imaging unit 326. The light separator 323 reflects the fluorescent light and the excitation light in the predetermined wavelength band or more (for example, 680 nm or more) to the optical path of the fluorescent light imaging unit 327. The white light of 400 to 680 nm that is reflected from the observed region 100 can be taken as an example of the white light in the wavelength band less than the predetermined wavelength. For example, the excitation light of 680 to 740 nm that is reflected from the observed region 100 and the fluorescent light of 760 to 850 nm that is generated from the observed region 100 can be taken as the excitation light and the fluorescent light in the predetermined wavelength band or more. On the other hand, if the light separator 323 is a half mirror, the light separator 323 reflects the light from the observed region 100 to the white light imaging unit 326 and the fluorescent light imaging unit 327 as in the case of the dichroic mirror.

The barrier filter 324 allows the fluorescent light from the observed region 100 to pass, and cuts off the light out of the wavelength band of the fluorescent light. Specifically, the barrier filter 324 cuts off reflected the light from the observed region 100 (for example, the excitation light in the wavelength band of 680 to 740 nm), out of the light from the observed region 100, that is reflected by the light separator 323 to the fluorescent light imaging unit 327, and allow the fluorescent light from the observed region 100 (for example, the fluorescent light of 760 to 850 nm) to pass to the fluorescent light imaging unit 327.

The imaging unit 325 includes the white light imaging unit 326 and the fluorescent light imaging unit 327. The imaging unit 325 has a function of capturing a white light image of the observed region 100 with the focus being on the observed region (in the focused state). The imaging unit 325 has a function of capturing the fluorescent light image of the observed region 100 in the focused state and the adjusted image of the observed region 100 in the unfocused state at the same timing.

The focus of the white light imaging unit 326 can be controlled by the image processing device 330 of the controller 339. The white light imaging unit 326 captures the white light image of the observed region 100 with the focus being on the observed region 100, and captures the adjusted image of the observed region 100 after the controller 339 controls the focus. Specifically, the white light imaging unit 326 includes an imaging device 326a, such as a CCD or COMS image sensor; and a movable optical system 326b, such as a lens, for forming an optical image of the object on the light receiver of the imaging device 326a.

As the imaging device 25a according to the first embodiment is, the imaging device 326a is a Bayer color imaging device that includes a group of color filters with different spectral properties arranged on the light receiver. The imaging device 326a receives the reflected light from the observed region 100 that is imaged by the movable optical system 326b via the color filter group, and performs the photoelectric conversion process on the received light with respect to each pixel of each color component in order to generate video signals of each color component of the observed region 100. When the white light from the light source device 310 is applied to the observed region 100, the imaging device 326a receives the white light from the observed region 100 that is imaged by the movable optical system 326b via the color filter group, thereby capturing the white light image or the adjusted image of the observed region 100. Each time the imaging device 326a captures a white light image or an adjusted image of the observed region 100, the imaging device 326a sequentially transmits video signals of each color component constituting the white light image or the adjusted image of the observed region 100 to the image acquiring unit 31 of the image processing device 330.

The movable optical system 326b is configured with an optical system, such as a lens, and a movable lens frame. The movable optical system 326b is driven and controlled by the controller 339 of the image processing device 330. Specifically, the movable optical system 326b is driven under the control of the controller 339, so that the relative distance between the imaging device 326a and the lens can be changed. The focus of the movable optical system 326b is controlled by the controller 339, and thus the movable optical system 326b can focus on the observed region 100. With the focus being on the observed region 100, the movable optical system 326b images the white light from the observed region 100, which is reflected by the light separator 323 to the optical path of the white light imaging unit 326, on the light receiver of the imaging device 326a. In this case, the imaging device 326a captures the white light image of the observed region 100 in the focused state.

The movable optical system 326b can shift the focus from the observed region 100 at a desired degree under the control of the controller 339. With the focus being shifted from the observed region 100 under the control of the controller 339, the movable optical system 326b images the white light from the observed region 100, which is reflected by the light separator 323 to the optical path of the white light imaging unit 326, on the light receiver of the imaging device 326a. In this case, the imaging device 326a captures the adjusted image that is the focus-controlled white light image of the observed region 100 after the focus control. Thereafter, the movable optical system 326b returns to the state where it focuses on the observed region 100 under the control of the controller 39. As in the case of the first embodiment, the gradation level of the adjusted image of the observed region 100 varies depending on the result of adjusting the focus of the movable optical system 326b under the control of the controller 339.

The fluorescent light imaging unit 327 is an imaging unit of which focus is fixed. The fluorescent light imaging unit 327 captures the fluorescent light image of the observed region 100 with the focus being on the observed region 100. Specifically, the fluorescent light imaging unit 327 includes an imaging device 327a, such as a CCD or a CMOS image sensor; and an optical system 327b, such as a lens, for forming a fluorescent light image of the object on the light receiver of the imaging device 327a.

The imaging device 327a is configured, for example, with a monochrome imaging device with higher sensitivity compared to the imaging device 326a of the white light imaging unit 326, and captures the fluorescent light image of the observed region 100. The imaging device 327a receives the fluorescent light from the observed region 100 that is imaged by the optical system 327b. With the focus being on the observed region 100, the optical system 327b images the fluorescent light from the observed region 100, which is reflected by the light separator 323 to the optical path of the fluorescent light imaging unit 327, and which passes through the barrier filter 324, on the light receiver of the imaging device 327a. The imaging device 327a performs the photoelectric conversion process on the fluorescent light with respect to each pixel in order to generate video signals of the observed region 100. When the white light from the light source device 310 is applied to the observed region 100, the imaging device 327a receives the fluorescent light from the observed region 100 that is imaged by the optical system 327b, thereby capturing the fluorescent light image. Each time the imaging device 327a captures a fluorescent light image of the observed region 100, the imaging device 327a sequentially transmits each video signal constituting the fluorescent light image of the observed region 100 to the image acquiring unit 31 of the image processing device 330.

In the third embodiment, the white light imaging unit 326 and the fluorescent light imaging unit 327 capture the images of the observed region 100 at the same timing under the control of the controller 339. Specifically, the fluorescent light imaging unit 327 captures the fluorescent light image of the observed region 100 at the timing same as that at which the white light imaging unit 326 captures the white light image or the adjusted image of the observed region 100. In other words, the positions of the subject coincide between the adjusted image of the observed region 100, which is captured by the white light imaging unit 326, and the fluorescent light image of the observed region 100, which is captured by the fluorescent light imaging unit 327.

The image processing device 330 includes the controller 339 as described above, and has a control function of causing the white light imaging unit 326 and the fluorescent light imaging unit 327 to perform the image capturing operations at the same timing. The image processing device 330 has functions similar to those of the image processing device 30 according to the first embodiment in addition to the function of the controller 339.

The controller 339 is configured with a storage unit 339a that stores predetermined process programs including an image processing program; and a computer that executes the process programs in the storage unit 339a. The storage unit 339a is a computer-readable storage medium according to the third embodiment. The controller 339 drives and controls the movable optical system 326b of the white light imaging unit 326 such that it focuses on the observed region 100 based on instruction information that is input by the input unit 38, and controls the imaging device 326a of the white light imaging unit 326 such that it captures the white light image of the observed region 100 in the focused state. The controller 339 also controls the focus of the white light imaging unit 326 by driving and controlling the movable optical system 326b such that it shifts the focus from the observed region 100 by the amount of a shift in accordance with the gradation level that is set by the gradation level setting unit 34. The controller 339 controls the imaging device 326a of the white light imaging unit 326 such that it captures the adjusted image of the observed region 100 in the unfocused state, and controls the imaging device 327a of the fluorescent light imaging unit 327 such that it captures the fluorescent light image of the observed region 100 in the focused state at the same timing at which the adjusted image is captured. Thereafter, the controller 339 drives and controls the movable optical system 326b such that it returns to the state where it focuses on the observed region 100. The controller 339 has functions similar to those of the controller 39 of the image processing device 30 according to the first embodiment in addition to the functions of controlling the white light imaging unit 326 and the fluorescent light imaging unit 327.

The controller 339 may control the imaging device 327a of the fluorescent light imaging unit 327 such that it does not captures the fluorescent light image of the observed region 100 at the timing at which the white light imaging unit 326 captures the white light image of the observed region 100 in the focused state, or may control the imaging device 327a of the fluorescent light imaging unit 327 such that it captures the fluorescent light image of the observed region 100 at the this timing. When the controller 339 causes the fluorescent light imaging unit 327 to capture a fluorescent light image at the timing same as that at which the white light image of the observed region 100 in the focused state is captured, the controller 339 may control the image acquiring unit 31 such that it deletes each video signal of the fluorescent light image at this timing.

Figure 10:
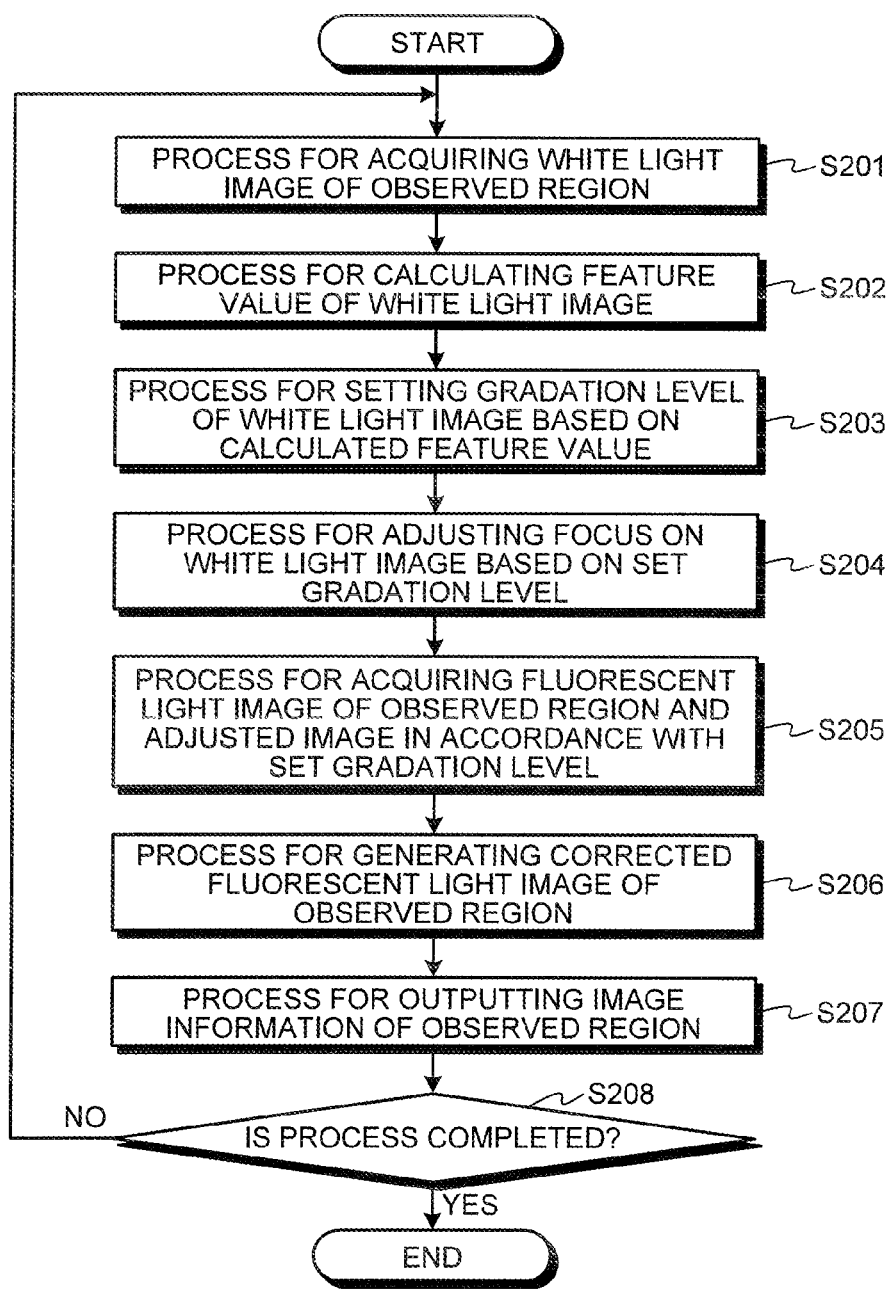
FIG. 10 is a flowchart illustrating a process procedure of an image processing device according to the third embodiment of the present invention.

The operations of the image processing device 330 according to the third embodiment of the present invention are explained below. FIG. 10 is a flowchart illustrating the process procedure of the image processing device according to the third embodiment of the present invention. The image processing device 330 according to the third embodiment performs the process procedure illustrated in FIG. 10 and displays and outputs the white light image and the fluorescent light image of the observed region 100.

In other words, as illustrated in FIG. 10, the image processing device 330 first acquires the white light image of the observed region 100 (step S201). At step S201, the controller 339 controls the light source device 310, the imaging system 328, and the image acquiring unit 31 such that the white light image of the observed region 100 that is being focused is acquired.

Under the control of the controller 339, the light source device 310 applies the white light in the wavelength band (for example, 440 to 740 nm) covering that of the excitation light to the observed region 100 because of the functions of the white light source 311 and the filter 314. The white light imaging unit 326 of the imaging system 328 focuses on the observed region 100 because the controller 339 drives and controls the movable optical system 326b. With the focus being on the observed region 100, the white light imaging unit 326 receives the white light that is reflected from the observed region 100, thereby capturing the white light image of the observed region 100. Under the control of the controller 339, the image acquiring unit 31 acquires each video signal of the white light image of the observed region 100 from the white light imaging unit 326, and transmits each acquired video signal to the storage unit 32 and the feature value calculator 33 after performing the above-described signal processes. The storage unit 32 stores each video signal of the white light image of the observed region 100 that is acquired from the image acquiring unit 31.

At step 201, the controller 339 may control the fluorescent light imaging unit 327 such that it does not capture the fluorescent light image of the observed region 100, or control the fluorescent light imaging unit 327 such that it captures the fluorescent light image of the observed region 100. When the controller 339 causes the fluorescent light imaging unit 327 to capture the fluorescent light image of the observed region 100 at step S201, the controller 339 may control the image acquiring unit 31 such that it deletes each video signal of the fluorescent light image or may cause the image output unit 37 such that it displays and outputs the fluorescent light image.

The image processing device 330 then performs the process for calculating the feature value of the white light image of the observed region 100 that is acquired at step S201 (step S202) as at step S103 according to the first embodiment illustrated in FIG. 4. Subsequently, the image processing device 330 performs the process for setting the gradation level of the white light image of the observed region 100 on the basis of the feature value calculated at step S202 (step S203) as at step S104 of the first embodiment illustrated in FIG. 4.

At step S202 and step S203, as in the case of the first embodiment, the controller 339 controls the feature value calculator 33 such that it calculates the feature value of the white light image of the observed region 100 that is acquired at step S201 and then controls the gradation level setting unit 34 such that it sets the gradation level of the white light image of the observed region 100 on the basis of the feature value calculated at step S202.

Subsequently, the image processing device 330 performs the process for adjusting the focus on the white light image of the observed region 100 on the basis of the gradation level set at step S203 (step S204). At step S204, the controller 339 calculates the amount of shift of the focus from the observed region 100 on the basis of the gradation level of the white light image of the observed region 100 that is set by the gradation level setting unit 34. The controller 339 controls the focus of the imaging system 328 such that the focus is shifted from the observed region 100 by the calculated shift amount.

Under the control of the controller 339, the white light imaging unit 326 of the imaging system 328 changes the relative distance between the imaging device 326a and the lens of the movable optical system 326b and shifts the focus from the observed region 100 by the shift amount in accordance with the gradation level that is set by the gradation level setting unit 34. At step S204, the fluorescent light imaging unit 327 keeps focusing on the observed region 100.

The image processing device 330 acquires the fluorescent light image of the observed region 100 and the adjusted image that is the white light image of the observed region 100 after the control of the focus on the observed region 100 in accordance with the set gradation level (step S205). At step S205, the controller 339 controls the light source device 310, the imaging system 328, and the image acquiring unit 31 such that the fluorescent light image of the observed region 100 being focused is acquired and the adjusted image of the observed region 10 not being focused in accordance with the gradation level set at step S203 is acquired.

Under the control of the controller 339, the light source device 310 applies again the white light in the wavelength band (for example, 400 to 740 nm) covering that of the excitation light to the observed region 100 because of the functions of the white light source 311 and the filter 314. With the focus being on the observed region 100, the fluorescent light imaging unit 327 of the imaging system 328 receives the fluorescent light, which is generated from the observed region 100 due to the excitation light in the white light, thereby capturing the fluorescent light image of the observed region 100. Simultaneously, with the focus that is adjusted at step S204, the white light imaging unit 326 of the imaging system 328 receives the white light that is reflected from the observed region 100, thereby capturing the adjusted image of the observed region 100. Under the control of the controller 339, the image acquiring unit 31 acquires each video signal of the fluorescent light image of the observed region 100, which is capture by the fluorescent light imaging unit 327, and each video signal of the adjusted image of the observed region 100, which is captured by the white light imaging unit 326 at the same timing as that of the fluorescent light image. The image acquiring unit 31 transmits each video signal, which is acquired from the fluorescent light imaging unit 327, to the storage unit 32 after performing the above-described signal processes. The storage unit 32 stores each video signal of the fluorescent light image, which is acquired from the image acquiring unit 31. The image acquiring unit 31 also transmits each video signal of the adjusted image of the observed region 100, which is acquired from the white light imaging unit 326, to the corrected fluorescent light image generator 35 after performing the above-described processes.

Subsequently, the image processing device 330 performs the process for generating the fluorescent light image of the observed region 100 (step S206) as at step S107 according to the first embodiment illustrated in FIG. 4, and then performs the process for outputting the image information of the observed region 100 (step S207) as at step S108 according to the first embodiment illustrated in FIG. 4.

At step S206, as in the case of the first embodiment, the controller 339 controls the corrected fluorescent light image generator 35 such that it generates the corrected fluorescent light image that is obtained by correcting the luminance value of the fluorescent light image of the observed region 100. At step S207, as in the case of the first embodiment, the controller 339 then controls the white light image generator 36 such that it generates the white light image of the observed region 100, and controls the image output unit 37 such that it displays the white light image and the corrected fluorescent light image of the observed region 100 to be output.

Thereafter, when a process completion operation, such as a predetermined off operation, is performed (YES at step S208) as at step S109 according to the first embodiment illustrated in FIG. 4, the image processing device 330 completes the process. In contrast, when the process completion operation is not performed (NO at step S209), the image processing device 330 goes back to step S201 and repeats the process procedure from step S201 and the following steps. In this case, the controller 339 performs the process procedure from step S201 to step S208 in order to appropriately control the light source device 310, the imaging system 328, and each constituent of the image processing device 330.

The adjusted image and the fluorescent light image of the observed region 100 that are acquired at step S205 are the information of the images of the observed region 100 that are captured at the same timing by the white light imaging unit 326 and the fluorescent light imaging unit 327. Thus, the positions of the object, such as the lesion 101, coincide between the adjusted image and the fluorescent light image. The corrected fluorescent light image generator 35 divides the luminance value of the fluorescent light image of the observed region 100 by the luminance value of the adjusted image, containing the object of which position coincides with that in the fluorescent light image, with respect to each corresponding pixel. Accordingly, the luminance value of the fluorescent light image of the observed region 100 can be corrected with high accuracy without influence of the shift of the position of the object between the images. As a result, the corrected fluorescent light image generator 35 can generate the corrected fluorescent light image of the observed region 100 that is obtained by correcting the luminance value with higher accuracy compared with the first embodiment.

As explained above, in the third embodiment, the fluorescent light image of the observed region to be observed and the adjusted image, which is the white light image of the observed region 100 captured after the focus control at the same timing at which the fluorescent light image is captured, are acquired first. By performing division regarding the fluorescent light image of the observed region using the acquired adjusted image, the corrected fluorescent light image, which is obtained by correcting the luminance value of the fluorescent light image, is generated. Other aspects of the configuration are similar to those of the first embodiment. Thus, functions and effects similar to those of the first embodiment can be achieved, and the positions of the object can coincide between the fluorescent light image and the adjusted image that are used for generating the corrected fluorescent light image. By use of the adjusted image containing the object of which position coincides with that in the fluorescent light image to be corrected, the luminance value of the fluorescent light image of the observed region can be corrected with higher accuracy without influence of the shift of the position of the object between the images.

By use of the image processing device, the imaging device, the computer-readable storage medium, and the image processing method according to the third embodiment, abnormal body tissue, such as a lesion, in the observed region can be drawn clearly with high accuracy in the fluorescent light image. This further increase the capability of detecting abnormal body tissue in the subject, using the fluorescent light image to be observed, and increases the diagnostic capability.

In the first embodiment, the feature value calculator 33 calculates the total luminance value of the entire edge, which is contained in the white light image of the observed region 100, as the edge information that is an example of the feature value of the white light image. Alternatively, the feature value calculator 33 may calculate the number of pixels of the entire edge, which is contained in the white light image of the observed region 100, as the edge information of the white light image. Alternatively, the feature value calculator 33 may previously stores a threshold relating to the pixel luminance value, compare each luminance value of the entire edge contained in the white light image of the observed region 100 with the threshold, and calculate the number of pixels of the edge with the luminance value of the threshold or higher as the edge information of the white light image. In this case, the data table 34a contains each range of the number of pixels serving as the edge information and gradation level that differs in each range of the number of pixels. With reference to the data table 34a, the gradation level setting unit 34 increases the gradation level of the white light image with an increase of the number of pixels serving as the edge information, and decreases the gradation level of the white light image with a decrease in the number of pixels serving as the edge information.

Figure 11:
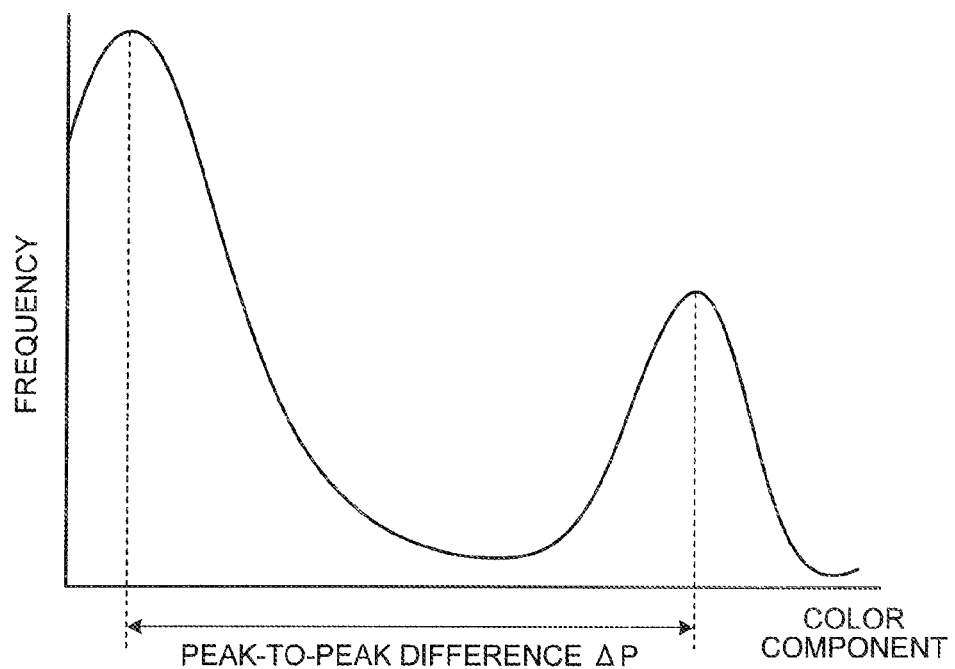
FIG. 11 is a schematic diagram representing an example of a peak-to-peak difference of the color distribution in a white light image of an observed region that can be calculated by a feature value calculator of the endoscope according to the second embodiment of the present invention.

In the second embodiment, the feature value calculator 233 calculates the dispersion, which represents the degree of dispersion of the detected color component (for example, the red color component) in the white light image of the observed region 100, as the color distribution information that is an example of the feature value of the white light image. Alternatively, the feature value calculator 233 may calculate the peak-to-peak difference of the color distribution in the white light image as the color distribution information of the white light image of the observed region 100. FIG. 11 is a schematic diagram representing an example of the peak-to-peak difference of the color distribution in the white light image of the observed region. Specifically, the feature value calculator 233 detects the color distribution of the predetermined color component (for example, the red color component) in the white light image of the observed region 100 and other color components (for example, the blue color component and the green color component) in the white light image on the basis of each video signal of the white light image. The feature value calculator 233 calculates a peak-to-peak difference $\Delta P$ (see FIG. 11) of the detected color distribution as the color distribution information of the white light image. In this case, the data table 234a contains each range of the peak-to-peak difference $\Delta P$ serving as the color distribution information and the gradation level that differs in each range of the peak-to-peak difference $\Delta P$. With reference to the data table 234a, the gradation level setting unit 234 reduces the gradation level of the white light image with an increase of the peak-to-peak difference ΔP serving as the color distribution information, and increases the gradation level of the white light image with a decrease of the peak-to-peak difference ΔP serving as the color distribution information.

The peak-to-peak difference ΔP of the detected color distribution represents the degree of concentration of the predetermined color in the white light image of the observed region 100. The degree of dispersion (dispersion) of the predetermined color in the white light image increase with an increase of the peak-to-peak difference ΔP, and the degree of concentration of the predetermined color in the white light image increases with a decrease of the peak-to-peak difference ΔP.

In the second embodiment, the case where the red color component is detected as the color distribution information of the white light image of the observed region 100. Alternatively, the color component that is detected as the color distribution information of the white light image of the observed region 100 may be the blue color component other than the red color component, for example, the greed color component, or other color components such as yellow, cyan, and magenta.

In the first and second embodiment, the fluorescent light image of the observed region 100 is acquired at step S102 illustrated in FIG. 4. Alternatively, the fluorescent light image of the observed region 100 to be corrected may be acquired at desired timing as long as the timing is before the process procedure of step S105, i.e., before the focus of the imaging unit 25 is shifted from the observed region 100.

Furthermore, in the first to third embodiments, the gradation level setting unit includes the data table that represents the relation between the feature value and the gradation level of the white light image, and sets the gradation level of the white light image with reference to the data table. Alternatively, the gradation level setting unit may previously store an equation of the gradation level that represents the relation between the feature value (for example, the edge information or the color distribution information of the white light image), which is calculated by the feature value calculator, and the gradation level of the white light image and may calculate the gradation level of the white light image on the basis of the equation of the gradation level and the feature value of the white light image that is acquired from the feature value calculator.

In the first to third embodiments, the controller calculates the amount of shift of the focus from the observed region on the basis of the gradation level of the white light image that is set by the gradation level setting unit. Alternatively, the process for calculating the shift amount of the focus, which is performed by the controller, may be based on an equation that is previously set in the controller, or may be based on a lookup table that is previously set in the controller.

In the first to third embodiments, the white light image of the observed region is generated in the process procedure at step S108 illustrated in FIG. 4 or step S207 illustrated in FIG. 10, i.e., in the process for outputting the image information of the observed region. Alternatively, the white light image of the observed region may be generated in a desired process procedure from capturing of the white light image until outputting of the white light image.

In the first to third embodiments, the focus on the observed region is controlled by driving and controlling the movable optical system. Alternatively, the focus on the observed region may be controlled by controlling the relative distance between the imaging device and the lens. For example, the focus on the observed region 100 may be controlled by fixing the optical system, such as a lens, and moving the imaging device in parallel, or may be controlled by moving both of the movable optical system and the imaging device.

In the first and second embodiments, the white light image and the fluorescent light image of the observed region 100 are captured alternately by the single imaging unit 25. Alternatively, a white light imaging unit, a fluorescent light imaging unit, and a light separator as those illustrated in the third embodiment may be arranged in the insertion unit 20, and a white light image and a fluorescent light image of the observed region 100 may be captured alternately by the white light imaging unit and the fluorescent light imaging unit. In this case, the wavelength band of the excitation light that is applied to the observed region 100 is not limited to that of visible light or less. Alternatively, the wavelength may be within the wavelength band of visible light or may be the wavelength band of visible light or more.

In the third embodiment, the edge information is calculated as the feature value of the white light image as in the case of the first embodiment. Alternatively, the color distribution information may be calculated as the feature value of the white light image as in the case of the second embodiment. In this case, it suffices that the image processing device 330 according to the third embodiment includes the feature value calculator 233 according to the second embodiment instead of the feature value calculator 33 and includes the gradation level setting unit 234 according to the second embodiment instead of the gradation level setting unit 34.

In the first to third embodiments, the white light is applied as an example of illuminating light to the observed region. Alternatively, the illuminating light that is applied to the observed region may be light of a desired color component, for example, red or green.

In the first to third embodiments, the white light image and the corrected fluorescent light image of the observed region are displayed on the image output unit 37. Alternatively, the image output unit 37 may be a printer that prints the white light image and the fluorescent light image of the observed region on a printing medium, such as paper. Alternatively, the image output unit 37 may be a storage device that includes a built-in storage medium, such as a hard disk, or a portable storage medium, such as a memory card, and that stores the white light image and the fluorescent light image of the observed region in the storage medium.

In the first to third embodiments, the endoscope for observing a subject, such as body tissue, is explained as the imaging device according to the present invention. Alternatively, the imaging device according to the present invention may be an endoscope or a microscope that is used in fields other then the medical field. Alternatively, the imaging device may be an imaging device other than endoscopes and microscopes, such as a digital camera or a digital video camera, or a portable information terminal device, such as a mobile phone with an imaging function. The image processing device according to the present invention is not limited to those incorporated in medical endoscopes. The image processing device may be incorporated in an endoscope or a microscope used in fields other than the medical field. Alternatively, the image processing device may be incorporated in imaging devices, such as a digital camera or a digital video camera, other than endoscopes or microscopes used in the medical field, or may be incorporated in a portable information terminal device, such as a mobile phone with an imaging function.

In the first to third embodiments, the process procedure of the image processing device by software based on operations of the controller that executes the process programs is explained. Alternatively, the image processing device according to the present invention may perform the process procedure by hardware. The computer readable storage medium of each embodiment stores the image processing program for performing the image processing according to the image processing method of the embodiment. The storage medium may be a built-in storage medium, such as a hard disk, or a portable storage medium, such as a memory card.

The image processing devices, the imaging devices, the computer readable storage media, and the image processing methods according to the embodiments accurately correct the luminance of the fluorescent light image of the observed region without influence of the line object in the observed region.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing method, comprising:
    acquiring a reflected light image of an observed region based on light that is reflected from the observed region;
    calculating a feature value of the reflected light image;
    setting an amount of shift of focus of the reflected light image on the basis of the feature value;
    controlling a focus of an imaging system for the reflected light image in accordance with the amount of shift of focus;
    acquiring a focus-controlled reflected light image of the observed region when the focus is controlled to be in an unfocused state; and
    generating a corrected fluorescent light image that is obtained by correcting a fluorescent light image of the observed region, using the focus-controlled reflected light image that is in the unfocused state;
    wherein the focus of the imaging system is controlled so that the focus-controlled reflected light image arrives at the unfocused state in the observed region in accordance with the amount of shift of focus.

2. The image processing method according to claim 1, wherein
    as the feature value of the reflected light image, at least one of edge information of the reflected light image, a dispersion of a predetermined color component that is contained in the reflected light image, and a peak-to-peak difference of a color distribution of the reflected light image is calculated, and
    after the focus of the imaging system is controlled in accordance with the amount of shift of focus, the focus-controlled reflected light image of the observed region is acquired.

3. The image processing method according to claim 1, wherein division regarding the fluorescent light image is performed using the focus-controlled reflected light image of the observed region, in order to generate the corrected fluorescent light image that is obtained by correcting a luminance value of the fluorescent light image.

4. The image processing method according to claim 1, wherein
    the feature value includes edge information of the reflected light image, and
    the amount of shift of focus of the reflected light image is increased with an increase of the edge information, and the amount of shift of focus of the reflected light image is reduced with a decrease of the edge information.

5. The image processing method according to claim 1, wherein
    the feature value includes a dispersion of a predetermined color component that is contained in the reflected light image, and
    the amount of shift of focus of the reflected light image is increased with an increase of the dispersion of the predetermined color component, and the amount of shift of focus of the reflected light image is reduced with a decrease of the dispersion of the predetermined color component.

6. The image processing method according to claim 1, wherein
    the feature value includes a peak-to-peak difference of a color distribution of the reflected light image, and
    the amount of shift of focus of the reflected light image is increased with an increase of the peak-to-peak difference of the color distribution, and the amount of shift of focus of the reflected light image is reduced with a decrease of the peak-to-peak difference of the color distribution.

7. The image processing method according to claim 1, wherein
    the reflected light image and the fluorescent light image are sequentially captured by the imaging system, with the focus being on the observed region, and
    the focus-controlled reflected light image is captured after the focus is controlled in accordance with the amount of shift of focus.

* * * * *